United States Patent
Li et al.

(10) Patent No.: US 7,250,423 B2
(45) Date of Patent: Jul. 31, 2007

(54) METHODS FOR SYNTHESIZING HETEROCYCLES AND THERAPEUTIC USE OF THE HETEROCYCLES FOR CANCERS

(76) Inventors: Chao-Jun Li, 4901 Lake Como, Metairie, LA (US) 70006; Jianheng Zhang, 929 Tamarack La., Apt. 6, Sunnyvale, CA (US) 94086

( * ) Notice: Subject to any disclaimer, the term of this patent is extended or adjusted under 35 U.S.C. 154(b) by 0 days.

(21) Appl. No.: 10/254,033

(22) Filed: Sep. 24, 2002

(65) Prior Publication Data
US 2003/0149069 A1 Aug. 7, 2003

Related U.S. Application Data

(60) Provisional application No. 60/324,392, filed on Sep. 24, 2001.

(51) Int. Cl.
*A61K 31/4355* (2006.01)
*A61K 31/436* (2006.01)
*C07D 491/48* (2006.01)
*C07D 491/52* (2006.01)

(52) U.S. Cl. ............... 514/291; 546/80; 546/89
(58) Field of Classification Search ............ 546/89, 546/80; 514/291
See application file for complete search history.

(56) References Cited

U.S. PATENT DOCUMENTS 3,419,561 A * 12/1968 Jenkins ............... 546/89
5,565,324 A * 10/1996 Still et al. ............ 435/6
6,180,640 B1 * 1/2001 Cuny et al. ............ 514/291

FOREIGN PATENT DOCUMENTS

| WO | WO 98/27093 | * | 6/1998 |
| WO | WO 99/67238 | * | 12/1999 |
| WO | WO2004/072046 | * | 8/2004 |
| WO | WO2005/016255 | * | 2/2005 |

OTHER PUBLICATIONS

Sof'ina et al. Experimental Evaluation of Antitumor Drugs in the USA and USSR and Clinical Correlations. NCI Monograph 55. NIH Publication No. 80-1933. Dec. 1980. pp. 76-78.*
Banker et al. 'Modern Pharmaceutics'. Third Edition. Marcel Dekker, New York, 1996, p. 596.*
Wolff ME. 'Burger's Medicinal Chemistry and Drug Discovery'. Fifth Edition. vol. 1: Principles and Practice. John Wiley & Sons, New York, 1995, pp. 975-977.*

* cited by examiner

*Primary Examiner*—Rita Desai

(57) ABSTRACT

The present invention provides methods for synthesizing novel tetrahydroquinoline derivatives that are useful for cancer chemotherapy and anti-viral applications. The present invention provides compounds useful for cancer chemotherapy and methods for the preparation of these compounds. The present invention also includes cancer chemotherapy methods.

4 Claims, No Drawings

METHODS FOR SYNTHESIZING HETEROCYCLES AND THERAPEUTIC USE OF THE HETEROCYCLES FOR CANCERS

CROSS-REFERENCE TO RELATED APPLICATIONS

This application is based on and claims priority of our U.S. provisional application Ser. No. 60/324,392, filed Sep. 24, 2001, incorporated herein by reference in full.

STATEMENT REGARDING FEDERALLY SPONSORED RESEARCH OR DEVELOPMENT

This invention was made with partial government support under grant numbers CHE-9733256 from the National Science Foundation. The U.S. government has certain rights in this invention.

REFERENCE TO A "MICROFICHE APPENDIX"

Not applicable

BACKGROUND OF THE INVENTION

1. Field of the Invention

The invention relates to the synthesis of tetrahydroquinoline derivatives and their use in the treatment of various carcinomas.

2. General Background of the Invention

U.S. Pat. No. 6,077,862, incorporated herein by reference, provides an excellent background for the cancer chemotherapeutic use of the this invention.

Chemotherapeutic approaches are most effective to fight cancers with large growth factors, i.e., ones whose cells are rapidly dividing. Ideally cytotoxic agents that have specificity to recognize certain cancer and tumor cells while not affecting normal cells or other less malign tumor cells would be extremely desirable. Unfortunately, none have been found and instead agents that target especially rapidly dividing cells (both tumor and normal) have been generally used.

Clearly, the development of agents that would target certain cancer cells due to some unique specificity for them would be a breakthrough.

Tetrahydroquinoline moiety is present in various natural products and many tetrahydroquinoline derivatives bearing simple or complex substituents exhibit a broad range of biological activities[1] Therefore, it has been attracted researchers continuously to develop methods for the synthesis of tetrahydroquinoline derivatives.[2] Among the various methods, Lewis acid catalyzed aza-Diels-Alder reaction of N-arylimines with various dienophiles is one of the most powerful tools for constructing 2,3,4-substituted tetrahydroquinoline derivatives.[3] When cyclic enol ethers, such as 2,3-dihydrofuran or 3,4-dihydro-2H-pyran, are employed as dienophiles, tricyclic compounds (furano or pyrano quinoline derivatives) are obtained.[4] A one-pot procedure for synthesizing such compounds, based on the three components reaction of a substituted aniline, an aryl aldehyde and an electron-rich olefin in the presence of Lewis acid catalysts, has been reported recently.[5] Since this reaction is much efficient with aryl-aldimines than with alkyl-aldimines, various 2-aryl-tetrahydroquinolines have been synthesized and only a few examples of 2-substituted tetrahydroquinoline derivatives were reported. No procedure was available to synthesize 2-substituted tetrahydroquinoline derivatives via a simple and direct coupling between an aniline derivative and a cyclic enol ether or a cyclic hemiacetal (or its equivalent).

Due to the above-mentioned problems in the art, the present inventors have sought improvements and provide such improvements herein.

SUMMARY OF THE INVENTION

The present invention relates to tetrahydroquinoline derivatives and their use for the treatment of cancer or a viral infection in warm blooded animals, particularly in humans and other mammals. The methods may use such a compound in combination with a potentiator or a chemotherapeutic agent. The present invention also relates to methods for preparation of such compounds.

The compounds of the present invention are represented by the following formula A: ##STR1##

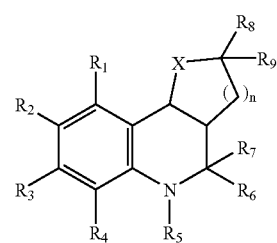

Structure 1 wherein

R1, R2, R3, R4, R5, R6, R7, R8, and R9 are each independently selected from the group consisting of hydrogen, alkyl, cycloalkyl, heterocycloalkylaryl, heteroaryl, acyl, acylalkyl, carboxy, carboxamido, trialkylsilyl, aryldialkyl, hydroxy, alkoxy, aryloxy, heteroaryloxy, chloro, bromo, fluoro, iodo, thio, alkylthio, arylthio, acyclthio, amino, alkylamino, dialkylamino, acylamino, arylamino, diarylamino, carboxamido; the number n ranges from 0 to 4; the X can be —O—, —S—, —S(O)—, —S(O$_2$)—, —CH2-, —NR10- where R10 is selected from the group consisting of hydrogen, alkyl, cycloalkyl, heterocycloalkylaryl, heteroaryl, acyl, acylalkyl, carboxy, carboxamido, trialkylsilyl, aryldialkyl; or connected to a polymer.

Pharmaceutically acceptable salts of the tetrhydroquinoline derivatives of Structure 1 are also included in the present invention. Further included in the invention are the prodrugs of the compounds of formula A: ##STR2##

In one embodiment of the invention, the tetrahydroquinoline derivatives of the invention are of the formula A-1: ##STR2##

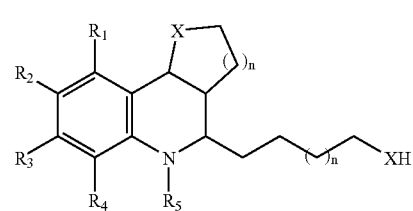

Structure 2 and preferably the compounds are of formula A-1 where R1, R2, R3, and R4 is an amino, alkylamino, dialkylamino, cycloalkylamino, heterocycloalkylamino, acylamino, arylamino, diarylamino, carboxamido group; R5 is a hydrogen, alkyl, akenyl, aryl, alkynyl, aryl, and carboxyl group; n is 1 or 2; and X is a selection of —O—, —S—, or —NR—, where R is hydrogen, alkyl, akenyl, aryl, alkynyl, aryl, and carboxyl group.

In another embodiment of the invention, the tetrahydroquinoline derivatives are of the formula A-2 where R2 is hydroxyl, alkylamino, dialkylamino, cycloalkylamino, heterocycloalkylamino, acylamino, arylamino, diarylamino, carboxamido group; and n is 1 or 2: ##STR3##

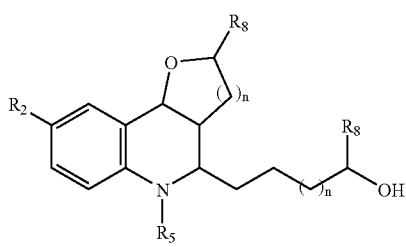

Structure 3

In another embodiment of the invention, the tetrahydroquinoline derivatives are of the formula A-3: ##STR4##

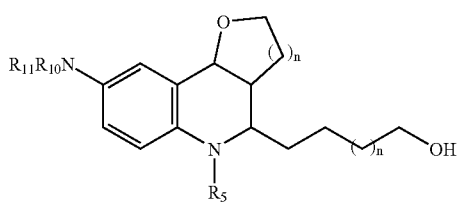

Structure 4 and preferably the compounds are of formula A-3 where R11, R12, and R5 is a hydrogen, alkyl, akenyl, aryl, alkynyl, aryl, and carboxyl group, or R11 and R12 are connected to form a ring of 3 to 10 atoms; n is 1 or 2;

In another embodiment of the invention, the tetrahydroquinoline derivatives are of the formula A-4: ##STR5##

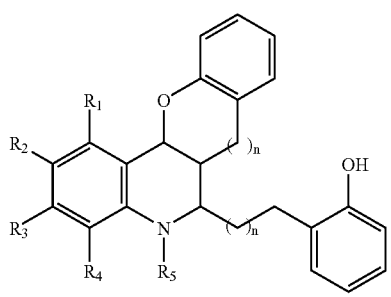

Structure 5 where R1, R2, R3, and R4 is an amino, alkylamino, dialkylamino, cycloalkylamino, heterocycloalkylamino, acylamino, arylamino, diarylamino, carboxamido group; R5 is a hydrogen, alkyl, akenyl, aryl, alkynyl, aryl, and carboxyl group; n is 0 or 1.

In another embodiment of the invention, the tetrahydroquinoline derivatives are of the formula A-5: ##STR6##

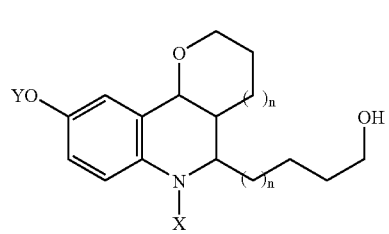

Structure 6 where X and Y are each independently a selection of hydrogen, alkyl, akenyl, aryl, alkynyl, aryl, and carboxyl group; n is 0 or 1.

Methods for synthesizing these compounds of the present invention involve the combining certain aniline derivatives include aniline with a cyclic enol ethers, or cyclic hemiacetals or their chemical equivalents. The process is also suitable for the rapid generation of combinatorial libraries of tetrahydroquinoline derivatives.

The synthetic procedure is quite simple and works in a variety of solvents including but not limited to water, ethanol, dichloromethane, or without solvent. Polymer and solid supported synthesis of tetrahydroquinoline derivatives are also possible by this method. Stereoselective formation of the compounds is also possible when certain chiral components are used in the reaction. Due to its simplicity and the fact that hazardous chemicals and special precautions are not required, this invention is suitable for the practical and convenient synthesis of many related analogs including stereochemically pure derivatives. In this manner, this invention is useful for the preparation of various pharmaceuticals and agrochemicals.

One aspect of the invention is a process of generating tetrahydroquinoline derivatives by reacting aniline derivatives with cyclic enol ethers or cyclic hemiacetals and they chemical equivalents under mild conditions.

DETAILED DESCRIPTION OF THE INVENTION

A. Definitions

The term "alkyl" refers to a fully saturated monovalent hydrocarbon radical of 1 to 12 carbon atoms. It may be straight-chain or branched. Preferred are those alkyl groups containing 1 to 10 carbon atoms, with 2 to 8 carbon atoms particularly preferred.

The term "alkenyl" refers to an unsaturated monovalent hydrocarbon radical of 2 to 12 carbon atoms containing only carbon and hydrogen and having one or more double bonds. It may be straight-chain or branched. Preferred are those alkenyl groups containing 2 to 10 carbon atoms, with 2 to 8 carbon atoms particularly preferred.

The term "alkoxy" means the group —OR' wherein R' is alkyl. Preferred are alkoxy groups having 1 to 10 carbon atoms, more preferably 2 to 8 carbon atoms.

The term "alkoxyalkyl" refers to an alkoxy group covalently attached to an alkyl group. The alkoxy group contains from 1 to 12, preferably from 1 to 6 carbon atoms. The alkoxy group may be substituted with one or more hydroxyl groups (an "hydroxyalkoxyalkyl") or with one or more halogen atoms (a "haloalkoxyalkyl"); preferably the hydroxyl or halogen is on the terminal end of the alkoxyalkyl substituent "Heterocyclo" designates a heterocyclic group; that is, a closed-ring structure, usually of either 5 or 6 members, in which one or more of the atoms in the ring is an element other than carbon, such as for example sulfur, nitrogen, or oxygen. A heterocyclic group may be, but is not limited to, pyridine, pyrrole, furan, thiophene, morpholine, and purine, optionally substituted with one or more nitro, carboxy, sulfonic acid, hydroxy, alkyl, alkoxy, or halide substituents.

The term "amino" refers to primary amines (—NH.sub.2), secondary amines (—NHR'), and tertiary amines (—NR'R"), where R' and R" are the same or different substituent groups, such as alkyl, alkenyl, halogen, hydroxy, and the like.

"Independently" signifies that two or more of the groups immediately preceding the term are either identical or different; i.e., selection of one from the list following the term does not affect selection of the other(s).

"Substituted" encompasses both single and multiple substitutions, the latter including multiple substitutions by the same substituent as well as mixtures of different substituents.

As used herein, a "pharmaceutical addition salt" or "pharmaceutically acceptable salt" is a salt of the tetrahydroquinolinederivative compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and others known to those of ordinary skill in the art.

As used herein, the term "prodrug" refers to a form of a tetrahydroquinolinederivative compound that has minimal therapeutic activity until it is converted to its desired biologically active form. A prodrug is a compound having one or more functional groups or carriers covalently bound thereto, which functional groups or carriers are removed from the compound by metabolic processes within the body to form the respective bioactive compound.

As used herein, the term "metabolite" refers to the breakdown or end product of a tetrahydroquinoline derivative compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a tetrahydroquinoline derivative compound or its salt may be the biologically active form of the compound in the body. An assay for activity of a metabolite of a tetrahydroquinoline derivative of the present invention is known to one of skill in the art in light of the present disclosure, for example, testing for efficacy against a virus in vitro or in vivo.

As used herein, "cancer" refers to all types of cancers, or neoplasms or benign or malignant tumors. In one embodiment, those cancers that attack normal healthy blood cells or bone marrow are contemplated by the present invention. Preferred cancers for treatment using methods provided herein include carcinoma, sarcoma, lymphoma, or leukemia. By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma. A preferred host is a human host.

A "viral infection" as used herein means an infection due to a DNA virus or an RNA virus (retrovirus). Examples of a double-stranded DNA virus are the Herpes virus and the influenza virus. Human immunodeficiency virus (HIV) is a prototype for retroviruses, i.e., viruses that use reverse transcription to replicate. However, certain DNA viruses use, in part, reverse transcription mechanisms to replicate such as, for example, the Hepatitus B virus. "Viruses" include retroviruses such as HIV or HTLV, influenza, rhinoviruses, herpes, hepatitis, or the like.

As used herein, a tetrahydroquinoline derivative of formulas A and A-1 through A-4, or a pharmaceutical salt thereof or a prodrug thereof, are "compounds of the present invention." Such compounds are further set forth under B infra.

As used herein, "potentiators" are materials that affect the immune system or enhance the effectiveness of a compound of the present invention and are further set forth under E herein.

Following long-standing patent law convention, the terms "a" and "an" mean "one or more" when used in this application, including the claims.

B. Tetrahydroquinoline Derivatives

The tetrahydroquinoline derivatives of the present invention are those of formula A, as set forth above. Presently preferred compounds are those of formulas A-1 through A-4.

Pharmaceutically acceptable salts of the tetrahydroquinoline compounds are considered within the scope of compounds of the present invention. They are salts with an organic or inorganic acid. Preferred acid addition salts are chlorides, bromides, sulfates, nitrates, phosphates, sulfonates, formates, tartrates, maleates, malates, citrates, benzoates, salicylates, ascorbates, or the like. Such salts may be synthesized from the compound of the present invention, or derivative thereof, that contains a basic or acidic moiety, by conventional chemical methods. Generally, such salts may be prepared by reacting a free acid or base form of the compound, or derivative thereof, with a stoichiometric amount of the appropriate base or acid in water or in an organic solvent, or in a mixture of the two.

Pharmaceutically acceptable salts of the compounds of the present invention include conventional non-toxic salts or the quaternary ammonium salts of the compounds or derivatives formed, for example, from non-toxic inorganic or organic acids. For example, such conventional non-toxic salts include those derived from inorganic acids such as hydrochloric, hydrobromic, sulfuric, sulfamic, phosphoric, nitric, or the like; and salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, or the like. Preferred acid addition salts are chlorides, bromides, sulfates, nitrates, phosphates, sulfonates, formates, tartrates, maleates, malates, citrates, benzoates, salicylates, ascorbates, or the like. A presently preferred salt is the hydrochloride salt.

Further included within the scope of the compound, or salts thereof, useful for the present invention are prodrugs thereof. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. Prodrugs include compounds wherein hydroxy, amine, or thio groups are bonded to any group that, when administered to a mammalian subject, is cleaved to form a free hydroxyl, amino, or thio group, respectively. Examples of prodrugs include, but are not limited to, acetate, formate, or benzoate derivatives of alcohol or amine functional groups in the compounds of the present invention; phosphate esters, dimethylglycine esters, aminoalkylbenzyl esters, aminoalkyl esters or carboxyalkyl esters of alcohol or phenol functional groups in the compounds of the present invention; or the like.

Synthetic Reaction Parameters

The reaction temperature can vary widely depending on the reactivity of the reactants. However, the temperature should not be so high as to decompose the reactants or so low as to cause inhibition of the condensation or freezing of the solvent. Unless specified to the contrary, the reactions described herein take place at atmospheric pressure over a temperature range from the temperature of dry ice to about 100.degree. C., more preferably from about 10.degree. C. to about 50.degree. C.

Unless otherwise specified, the reaction times and conditions are intended to be approximate.

The time required for the reactions herein will depend to a large extent on the temperature being used and the relative reactivities of the starting materials. Therefore, the reaction time can vary greatly, for example from about five minutes to about two days. Various known techniques such as different types of chromatography, especially thin layer chromatography ("TLC"), gas chromatography ("GC"), or optical spectroscopy can be used to follow the progress of the reaction by the disappearance of the starting compound(s).

Isolation and purification of the compounds and intermediates described herein can be effected, if desired, by any suitable separation or purification procedure such as, for example, distillation, filtration, extraction, crystallization, column chromatography, thin-layer chromatography, thick-layer chromatography, centrifugal chromatography, or preparatory HPLC, or a combination of these procedures. Specific illustrations of suitable separation and isolation procedures can be found by reference to the examples herein below. However, other equivalent separation or isolation procedures can, of course, also be used.

Synthesis of Compounds of Formula A

The compounds of the invention are prepared by reacting aniline derivatives with cyclic enol ethers, cyclic thioenolethers, cyclic amines, cyclic hemiacetals, cyclic hemiacetals, cyclic aminols, and their chemical equivalents in the presence of a Lewis acid for the present invention (Reaction Scheme 1, wherein X=O, S, NR10 where R10 is selected from the group consisting of hydrogen, alkyl, cycloalkyl, heterocycloalkylaryl, heteroaryl, acyl, acylalkyl, carboxy, carboxamido, trialkylsilyl, aryldialkyl; Y=HO, alkoxyl, aryloxy, heteroaryloxy, alkenoxy, alkynoxy, carboxyl, chloro, bromo, iodo, fluoro, trialkylsiloxy, thio, alkylsulfuryl, arylsulfuryl, alkylsulfoxyl, arylsulfoxyl, alkylsulfonyl, arylsulfonyl, alkylphosphoryl, arylphosphoryl, amino, alkylamino, arylamino, or carboxamino).

Scheme 1

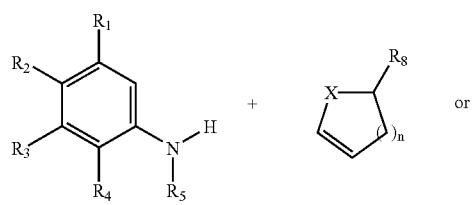

or

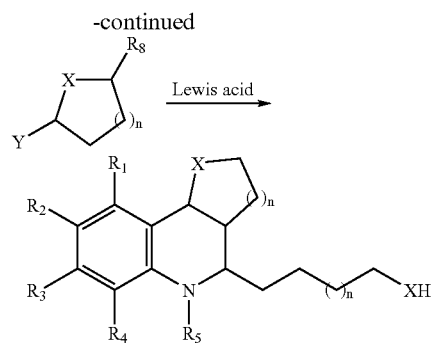

In one synthetic process, aniline is mixed with 2,3-dihydrofuran or dihydropyran and a catalytic amount of indium chloride in aqueous medium to form compounds of formula A-1 to A-3 (Reaction Scheme 2), following procedures known to those of skill in the art.

Scheme 2

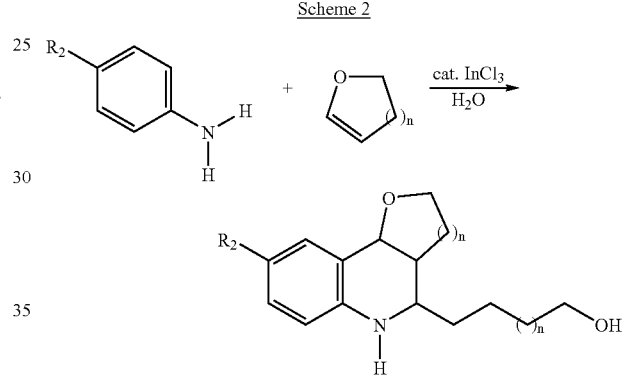

Alternatively, aniline is mixed with 2-hydroxyltetrahydrofuran or 2-hydroxyltetrahydropyran and a catalytic amount of indium chloride to form compounds of formula A-1 to A-3 (Reaction Scheme 3), following procedures known to those of skill in the art.

Scheme 3

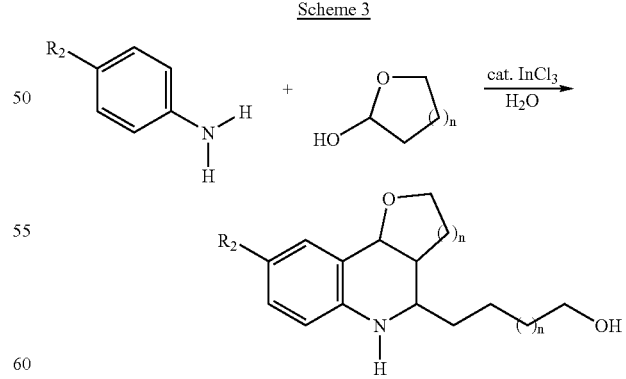

In a similar manner, to prepare compounds of Formula A-1 to A-3, aniline derivatives are reacted with 2-chromanol to give tetrahydroquinoline derivatives of formula A-4 (Reaction Scheme 4), following procedures known to those of skill in the art.

Scheme 4

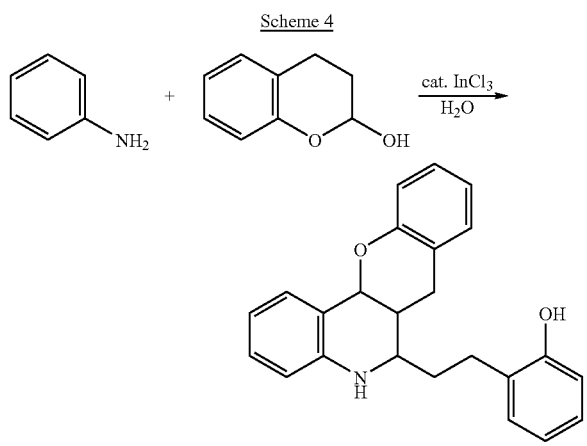

PRESENTLY PREFERRED EMBODIMENTS

In one embodiment of the present invention, presently preferred tetrahydroquinoline derivatives are those of Formula A-3 where n is 1 or 2, and R5, R10, R11 is selected from those groups listed in Table 1.

TABLE 1

| Cpd. No. | R5 | R10 | R11 | n |
|---|---|---|---|---|
| 3-1 | H | Ph | H | 2 |
| 3-2 | H | Ph | H | 1 |
| 3-3 | H | Me | Me | 1 |

In another embodiment of the invention, presently preferred tetrahydroquinolinederivatives are those of Formula A-4 where R is a hydrogen and n is 1 (cpd. No. 4-1).

In another embodiment of the invention, presently preferred tetrahydroquinolinederivatives are those of Formula A-4 where X and Y are hydrogen and n is 1 (cpd. No. 5-1).

C. Screening Assays

Screening assays for determining those cancers susceptible to treatment using compounds of the present invention include incubating cell line models representing specific cancers as set forth, for example, by the National Cancer Institute, in the presence and absence of such compounds.

Exemplary cell line models representing specific cancers include, but are not limited to, the following:

Non-small cell lung cancer: NCIH23, NCIH324, NCIH522, A549/ATCC, A549(ASC), CALU1, EKVX, NCIH125M, NCIH226, NCIH520, SKMES1, NCIH322M, NCIH358M, NCIH460, NCIH292, HOP62, HOP18, HOP19, HOP92, LXFL 529, SW1573, LXFS 650L, ML1019, ML1076, ML1045, or UABLG22;

Small cell lung cancer: NCIH69, NCIH146, NCIH82, NCIH524, DMS 114, DMS 273, HOP27, SHP77, or RHOS;

Colon cancer: HT29, HCC2998, HCT116, LOVO, SW1116, SW620, COLO 205, DLD1, WIDR, COLO 320DM, HCT15, CXF 280, KM12, KM20L2, COLO 741, CXF 264L, COLO 746, UABC02, MLI059, CAC02, HT29/PAR, HT29/MDR1, or NB4;

Breast cancer: MCF7, MCF7/ADRRES, ZR751, ZR7530, MDAMB231/ATCC, HS 578T, UISOBCA1, MCF7/ATCC, SKBR3, MDAMB435, MDAN, BT549, T47D, MDAMB231, MAXF 401, BT474, or MDAMB468;

Ovarian cancer: OVCAR3, OVCAR4, OVCAR5, OVCAR8, A2780, IGROV1, SKOV3, OVXF 899, A1336, or ES2;

Leukemia: P388, P3888/ADR, CCRFCEM, CCRFSB, K562, MOLT4, L1210, HL60(TB), RPMI8226, SR, or K562/ADR;

Fibroblast: IMR90, or CCD19LU;

Renal cancer: UO31, SN12C, SN12S1, SN12K1, SN12L1, SN12A1, A498, A704, CAKI1, RXF 393, RXF631, 7860, SW156, TK164, 769P, SS78, ACHN, TK10, RXF 486L, UOK57, or UOK57LN;

Melanoma: LOX IMVI, MALME3M, RPM17951, SKMEL2, SKMEL5, SKMEL28, SKMEL31, UCSD 242L, UCSD 354L, M14, M19MEL, UACC62, UACC257, MEXF 514L, or UABMEL3;

Prostate cancer: PC3, PC3M, DU145, LNCAP, 1013L, UMSCP1, WIS, JE, RER, MRM, DHM, AG, RB, RVP, FC, WAE, DB/SMC, JCA1, ND1, WMF, TSUPR1, JECA, GDP, T10, WBW, RVP1, or WLL;

CNS cancer: SNB7, SNB19, SNB44, SNB56, SNB75, SNB78, U251, TE671, SF268, SF295, SF539, XF 498, SW 1088, SW 1783, U87 MG, SF767, SF763, A172, or SMSKCNY;

Bone/muscle: A204/ATCC, OHS, TE85, A673, CHA59, MHM 25, RH18, RH30, or RD; and

Lymphoma: AS283, HT, KD488, PA682, SUDHL7, RL, DB, SUDHL1, SUDHL4, SUDHL10, NUDUL1, or HUT 102.

D. Chemotherapeutic Agents

U.S. Pat. No. 6,077,862 provides an excellent background for the definition of "Chemotherapeutic Agents" of the this invention.

E. Potentiators

U.S. Pat. No. 6,077,862 provides an excellent background for the definition of "Potentiators" of the this invention.

F. Dosage

U.S. Pat. No. 6,077,862 provides an excellent background for the definition of "Dosage" of the this invention.

G. Formulations

U.S. Pat. No. 6,077,862 provides an excellent background for the definition of "Formulations" of the this invention.

H. Method Of Treatment

U.S. Pat. No. 6,077,862 provides an excellent background for the definition of "Method Of Treatment" of the this invention.

I. Combination Therapy

U.S. Pat. No. 6,077,862 provides an excellent background for the definition of "Combination Therapy" of the this invention.

J. Pharmaceutical Kits

U.S. Pat. No. 6,077,862 provides an excellent background for the definition of "Pharmaceutical Kits" of the this invention.

K. Studies

The following studies were performed to test the effectiveness of the tetrahydroquinoline derivatives of the present invention against certain cancers and viral infections.

Colon and Melanoma Tumor Cells Test:

The following cell culture tests were performed by the National Cancer Institute of the National Institute of Health.

The compounds listed below have been evaluated in the 3-cell line, one dose primary anticancer assay. The compounds which pass our criteria for activity in this assay will be scheduled automatically for evaluation against the full panel of 60 tumor cell lines. For the past 10 years, the Development Therapeutic Program (DTP), Division of Cancer Treatment and Diagnosis (DCTD), National Cancer Institute (NCI) has used an in vitro model consisting of 60 human tumor cell lines as the primary anticancer screen [Ref: J. Natl, Cancer Inst., 83:757-766, 1991]. An analysis of the data indicated that approximately 95% of the actives from the 60 cell line screen can be identified using only three cell lines. For this reason, the DTP has now begun using, as its primary anticancer assay, a 3-cell line panel consisting of the MCF7 (Breast), NCI-H460 (Lung), and SF-268 (CNS). This 3-cell line, one-dose assay has been in use by DTP for several years for the evaluation of combinatorial libraries and has proven to be an effective pre-screen. The inclusion of this assay in our decision-making process will allow for more detailed evaluation of agents which have exhibited some level of ability to inhibit the growth of human tumor cells in culture.

In the current protocol, each cell line is inoculated and preincubated on a microtiter plate. Test agents are then added at a single concentration and the culture incubated for 48 hours. End-point determinations are made with alamar blue (Biotechniques 21(5) 780-782 (1996)). Results for each test agent are reported as the percent of growth of the treated cells when compared to the untreated control cells. Compounds which reduce the growth of any one of the cell lines to approximately 32% or less (negative numbers indicate cell kill) are passed on for evaluation in the full panel of 60 cell lines over a 5-log dose range. The testing results of selected compounds are listed in Table 2.

TABLE 2

| | | Growth Percentage | | |
|---|---|---|---|---|
| Cpd. No. | Concentr. (units) | (Breast) MCF7 | (Non Small Cell Lung) NCI-H460 | (CNS) SF-268 |
| 3-1 | 1.000E−04 (Molar) | −1 | −1 | −1 |
| 3-2 | 1.000E−04 (Molar) | 0 | 57 | 22 |
| 3-3 | 1.000E−04 (Molar) | 7 | 100 | 77 |
| 4-1 | 1.000E−04 (Molar) | 0 | 0 | 0 |
| 5-1 | 1.000E−04 (Molar) | 0 | 29 | 2 |

Further 60 cell-line tests showed that cpd. No. 3-1 is highly potent and selectively killed cancer cells of EKVX (non-small cell lung cancer), SF-539 (CNS cancer), PC-3 and DU-145 (prostate cancer), MDA-MB-435 (breast cancer), and Delta cancer cell lines even at 1.000E-08 molar concentration; whereas showed very week effect against other cell lines.

On the other hand, cpd. No. 5-1 is highly selective for PC-3 (prostate cancer) and Delta cancer, and moderately selective for CCRF-CEM (and other leukemia cancer cells), as well as NCI-H522(non-samll cell lung cancer), HCT (colon cancer), and CAKI-1(renal cancer). The high selectivity for certain cancer cells observed with these compounds provides the possibility of killing cancer cells in the presence of other cells. It also provides the possibility of connecting more effective cancer-drugs such as Taxol to these compounds for more effective cancer chemotherapy.

It should also be noted that several of compounds synthesized showed moderate biological activities for anti-viral studies.

Methods for Synthesizing Compounds of Formula A #STR1#

Advantages and Improvements Over Existing Technology:

Although there are many known methods for the synthesis of tetrahydroquinoline derivatives due to the vital importance of these compounds, any conceptually new and practical method in this area is of special significance. The existing methods for synthesizing tetrahydroquinoline derivatives use highly reactive reagents such as titanium tetrachloride, which generally require anhydrous solvents (such as methylene chloride, a carcinogen) and inert gas atmosphere, and protection of protonic functional groups such as hydroxyl and amines. Thus, the existing methods have high cost, are environmentally unsafe and potentially hazardous. Due to shortcomings of the existing methods, no general and practical synthesis of compounds with Formula A is available. The present invention offers a number of advantages over existing methods for synthesizing tetrahydroquinoline derivatives, including:

1. This new method for tetrahydroquinoline synthesis allows to synthesize tetrahydroquinoline derivatives having the general Formula A that some has not been accessible via the existing methods.
2. This new method for tetrahydroquinoline synthesis is exceptionally environmentally friendly and practical. The reactions can be done in water or aqueous solvents at ambient temperature without using any toxic, hazardous or corrosive materials, such as strong acids, strong bases, organotin, or other highly corrosive reagents such as titanium tetrachloride. Also the reaction does not require an inert atmosphere, and can be done in the air. Furthermore, the reaction can be done without using additional solvent other than the reactants. For compounds with protonic functional groups such as hydroxyl, protection is not required, which shortens synthetic steps and saves the cost.
3. The method of the invention offers direct construction of these complicated of Formula A from simple aniline derivatives and cyclic enol ethers or cyclic hemiacetals or their chemical equivalents.
4. The present method is highly versatile, allowing a high degree of structural variation in all reacting components. Since the reaction involves an initial condensation between aniline derivatives with one equivalent of cyclic enol ethers or cyclic hemiacetals or their chemical equivalents, followed the reaction of the intermediate with another equivalent of enol ethers or cyclic hemiacetals or their chemical equivalents, the method allows the one-pot construction of tetrahydroquinoline derivatives from several readily available building blocks. For these reasons, this method is easily applicable to the solid or liquid phase combinatorial synthesis of tetrahydroquinoline derivatives.
5. Because two-carbon based stereogenic centers were formed during the reaction process, the method allows the synthesis of compounds with formula A with stereochemical control if a chiral component is present.
6. Because the reaction can be carried out in water, water soluble reagents can be used and water soluble tetrahydroquinoline derivatives can be generated, which are highly important for drug formulation and drug delivery.

EXAMPLES

The following examples are put forth so as to provide those of ordinary skill in the art with a complete disclosure and description of how to perform the processes of the present invention, and are not intended to limit the scope of what the inventors regards as their invention. Efforts have been made to ensure accuracy with respect to numbers used (e.g. amounts, temperature, etc.) but some experimental errors and deviations should be accounted for. Unless indicated otherwise, molecular weight is weight average molecular weight, temperature is in degrees centigrade, and pressure is at or near atmospheric.

Table II-V, summarize a number of reactions from some representative anilines derivatives, cyclic enol ethers and cyclic hemiacetals. Subsequently, representative experimental procedures and structural data of the obtained products are given.

TABLE II

Synthesis of tetrahrdroquinoline derivatives by the reaction of substituted anilines with 3,4-dihydro-2H-pyran

| entry | amine | Reaction Condition | Tetrohydroquinolines | Yield (%) |
|---|---|---|---|---|
| 1 | aniline | r.t. (3d) | (cis)/(trans) = 68:32 | 90 |
| 2 | aniline | 50° C./10 h | (cis)/(trans) = 62:38 | 85 |
| 3 | 4-Me-aniline | 50° C./10 h | (cis)/(trans) = 57:43 | 88 |
| 4 | 4-MeO-aniline | 50° C./10 h | (cis)/(trans) = 66:34 | 62 |
| 5 | 4-Cl-aniline | 50° C./48 h | (cis)/(trans) = 57:43 | 51 |
| 6 | 4-Br-aniline | 50° C./48 h | (cis)/(trans) = 49:51 | 36 |

TABLE II-continued

Synthesis of tetrahrdroquinoline derivatives by the reaction of substituted anilines with 3,4-dihydro-2H-pyran

| entry | amine | Reaction Condition | Tetrohydroquinolines | Yield (%) |
|---|---|---|---|---|
| 7 | 4-F-C6H4-NH2 | 50° C./4 h | [9-fluoro-tetrahydropyrano[3,2-c]quinoline with 4-hydroxybutyl substituent] (cis)/(trans) = 68:32 | 68 |
| 8 | 4-HO-C6H4-NH2 | 50° C./10 h | [9-hydroxy-tetrahydropyrano[3,2-c]quinoline with 4-hydroxybutyl substituent] (cis)/(trans) = 74:26 | 74 |
| 9 | 4-PhNH-C6H4-NH2 | r.t./10h | [9-phenylamino-tetrahydropyrano[3,2-c]quinoline with 4-hydroxybutyl substituent] (cis)/(trans) = 47:53 | 87 |
| 10 | 4-NC-C6H4-NH2 | 50° C./48 h | [9-cyano-tetrahydropyrano[3,2-c]quinoline with 4-hydroxybutyl substituent] (cis)/(trans) = 34:66 | 30 |

TABLE III

Synthesis of tetrahrdroquinolines by the reaction between aromatic amines and 2,3-dihydrofuran

| entry | amine | Reaction Condition | Tetrohydroquinolines | Yield (%) |
|---|---|---|---|---|
| 1 | C6H5-NH2 | r.t./8h | [tetrahydrofuro[3,2-c]quinoline with 3-hydroxypropyl substituent] (cis)/(trans) = 78:22 | 85 |

TABLE III-continued

Synthesis of tetrahrdroquinolines by the reaction between aromatic amines and 2,3-dihydrofuran

| entry | amine | Reaction Condition | Tetrohydroquinolines | Yield (%) |
|---|---|---|---|---|
| 2 | 4-Me-C6H4-NH2 | r.t./4h | (cis)/(trans) = 81:19 | 84 |
| 3 | 4-MeO-C6H4-NH2 | r.t./4h | (cis)/(trans) = 87:13 | 81 |
| 4 | 4-Cl-C6H4-NH2 | 45° C./10h | (cis)/(trans) = 74:26 | 77 |
| 5 | 4-Br-C6H4-NH2 | 45° C./10h | (cis)/(trans) = 87:13 | 81 |
| 6 | 4-F-C6H4-NH2 | r.t./10h | (cis)/(trans) = 86:14 | 85 |
| 7 | 4-HO-C6H4-NH2 | r.t./2h | (cis)/(trans) = 96:4 | 73 |
| 8 | 4-PhNH-C6H4-NH2 | r.t./10h | (cis)/(trans) = 86:14 | 65 |

TABLE III-continued

Synthesis of tetrahrdroquinolines by the reaction between aromatic amines and 2,3-dihydrofuran

| entry | amine | Reaction Condition | Tetrohydroquinolines | Yield (%) |
|---|---|---|---|---|
| 9 | 4-NC-C6H4-NH2 | r.t./24h | (tetrahydroquinoline product with CN substituent) (cis)/(trans) = 77:23 | 38 |
| 10 | 4-Me2N-C6H4-NH2 | r.t./5h | (tetrahydroquinoline product with Me2N substituent) (cis)/(trans) = 69:31 | 46 |

TABLE IV

Synthesis of phenanthridine derivatives and N-alkyl substituted tetrahrdroquinolines

| entry | Amine | Cyclic enol Ether | Reaction Condition | Product | Yield (%) |
|---|---|---|---|---|---|
| 1 | 1-naphthylamine | 3,4-dihydro-2H-pyran | 50° C./10h | (phenanthridine product, cis/trans = 30:70) | 65 |
| 2 | 1-naphthylamine | 2,3-dihydrofuran | r.t./5h | (phenanthridine product, cis/trans = 68:32) | 81 |
| 3 | N-methylaniline | 3,4-dihydro-2H-pyran | 50° C./24h | (N-methyl tetrahydroquinoline product, cis/trans = 40:60) | 60 |

TABLE IV-continued

Synthesis of phenanthridine derivatives and N-alkyl substituted tetrahrdroquinolines

| entry | Amine | Cyclic enol Ether | Reaction Condition | Product | Yield (%) |
|---|---|---|---|---|---|
| 4 | PhNHMe | furan | r.t./24h | [furano-tetrahydroquinoline, N-Me, propyl-OH side chain] (cis)/(trans) = 45:55 | 65 |
| 5 | PhNHC₂H₅ | dihydropyran | 50° C./24h | [pyrano-tetrahydroquinoline, N-C₂H₅, butyl-OH side chain] (cis)/(trans) = 18:62 | 35 |
| 6 | PhNHC₂H₅ | furan | r.t./48h | [furano-tetrahydroquinoline, N-C₂H₅, propyl-OH side chain] (cis)/(trans) = 17:83 | 32 |
| 7 | PhNH-n-C₄H₉ | dihydropyran | 50° C./48h | [pyrano-tetrahydroquinoline, N-n-C₄H₉, butyl-OH side chain] (cis)/(trans) = 16:84 | 33 |
| 8 | PhNH-n-C₄H₉ | furan | r.t./48h | [furano-tetrahydroquinoline, N-n-C₄H₉, propyl-OH side chain] (cis)/(trans) = 15:85 | 34 |

TABLE V

Synthesis of tetrahydroquinolines by reaction between aniline and 2-hydroxy cyclic ether in water

| 2-Hydroxy cyclic ether | Reaction conditions | Tetrahydroquinolines | | Yield (%) |
|---|---|---|---|---|
| $R_8$-[furan]-OH | | [furanoquinoline with $R_8$, OH, $R_8$ substituents] | | |
| $R_8$ | | Cis (R/S) | Trans (R/S) | |
| H | r.t. (24 h) | 46 | 54 | 86 |
| $CH_3$ | r.t. (10 h) | 52 (30/22) | 48 (22/26) | 88 |
| $C_2H_5$ | r.t. (10 h) | 52 (26/26) | 48 (20/28) | 81 |
| $C_7H_{15}$ | r.t. (24 h) | 45 (6/39) | 55 (49/6) | 41 |
| $C_6H_5$ | r.t. (24 h) | | | 51 |
| $R_8$-[pyran]-OH | | [pyranoquinoline with $R_8$, OH, $R_8$ substituents] | | |
| $R_8$ | | Cis (R/S) | Trans (R/S) | |
| H | r.t. (24 h) | 36 | 64 | 89 |
| $CH_3$ | r.t. (24 h) | 40 (7/33) | 60 (35/25) | 85 |
| $C_6H_{13}$ | r.t. (24 h) | 44 (6/38) | 56 (46/10) | 45 |
| $C_6H_5$ | r.t. (24 h) | | | 48 |

Procedure 1:

A mixture of aromatic amine (substituted anilines, 1-animonapnthalene, N-alkyl anilines) (2 mmol), cyclic enol ether (3,4-dihydro-2H-pyran and 2,3-dihrdrofuran) (4-6 mmol) and indium chloride (0.2-0.4 mmol) in water was stirred at room temperature or at 50-60° C., while the progress of reaction was monitored by TLC. After the reaction was completed, the reaction mixture was extracted with ethyl ether or methylene chloride (3×20 ml). Removal of solvent and flash column chromatography gave 1,2,3,4-tetrahydroquinoline derivatives.

Procedure 2:

The mixture of aniline derivative (2 mmol), 2-hydroxy cyclic ethers (4-6 mmol) and $InCl_3$ (0.2-0.4 mmol) in water (5 mL) was stirred at room temperature. The reaction was monitored by TLC. After the reaction was completed, the reaction mixture was extracted with ethyl ether (3×20 mL). Removal of solvent and flash column chromatography gave 1,2,3,4-tetrahydroquinoline derivatives.

Example 1

Synthesis of 2,3,3a,4,5,9b-hexahydro-4-(3-hydroxypropyl)-8-phenylamino-furano[3,2-c]quinoline (Formula 3-2)

The mixture of 4-(N-phenylamino)-aniline (2 mmol), 2,3-dihrdrofuran (4 mmol) and indium chloride (0.2-0.4 mmol) in water was stirred at room temperature for 10 h. TLC showed the completion of the reaction. The reaction mixture was extracted with diethyl ether (3×20 ml) and drived over $MgSO_4$. Removal of solvent and flash column chromatography on silica gel gave the 1,2,3,4-tetrahydroquinoline derivative 3-1 in 65% yield (cis/trans=86:14). IR (film): 3326, 2932, 1595, 1504, 1047 $cm^{-1}$. $^1$HNMR and —$^{13}$CNMR(DMSO-$d_6$/TMS): cis-isomer, 7.53(s, 1H, NH), 7.08(m, 2H, Ar—H), 6.85(s, 1H, Ar—H), 6.76(m, 3H, Ar—H), 6.58(m, 2H, Ar—H), 5.09(s, 1H, NH), 4.92(d, 9b-H, J=8.0 Hz), 4.50(t, 1H, OH, J=4.8 Hz), 3.60(m, 2H), 3.30(m, 2H), 3.23(m, 1H), 2.48(m, 1H), 1.35-1.85(m, 6H). 146.77, 141.62, 133.52, 129.66, 123.36, 122.18, 121.69, 118.01, 115.69, 114.66, 75.75, 66.39, 61.52, 52.58, 42.35, 31.03, 29.42, 24.21. trans-isomer, 7.60(s, 1H, NH), 7.08(m, 2H, Ar—H), 6.91(s, 1H, Ar—H), 6.76(m, 3H, Ar—H), 6.58(m, 2H, Ar—H), 5.42(s, 1H, NH), 4.50(t, 1H, OH, J=4.8 Hz), 4.35(d, 9b-H, J=6.0 Hz), 3.75(m, 2H), 3.60(m, 2H), 3.30(m, 2H), 3.55(m, 1H), 2.24(m, 1H), 1.35-1.85(m, 5H). 146.94, 141.75, 132.65, 129.66, 123.46, 122.59, 121.00, 118.01, 115.69, 114.58, 79.81, 65.39, 61.69, 52.34, 41.41, 30.10, 29.53, 29.07. Anal. Calcd. For $C_{20}H_{24}N_2O_2$: C, 74.05; H, 7.46; N, 8.63. Found: C, 73.84; H, 7.81; N, 8.56.

Procedure 2:

The mixture of 4-(N-phenylamino)-aniline (2 mmol), 2-hydroxy-tetrahydrofuran (6 mmol) and $InCl_3$ (0.2-0.4 mmol) in water (5 mL) was stirred at room temperature. The reaction was monitored by TLC. After 24 h stirring at room temperature, the reaction mixture was extracted with ethyl ether (3×20 mL). Removal of solvent and flash column chromatography gave 1,2,3,4-tetrahydroquinoline derivatives in 86% yield (cis:trans=46:54).

Example 2

Synthesis of 3,4,4a,5,6,10b-hexahydro-5-(4-hydroxybutyl)-9-phenylamino-2H-pyrano[3,2-c]quinoline(Compound 3-1)

Procedure 1:

Via general procedure 1, the titled compound was prepared from 4-(N-phenylamino)-aniline (2 mmol), 3,4-dihydropyran (4 mmol) and indium chloride (0.2-0.4 mmol) in water at room temperature for 10 h. Yield: 87%. Trans/cis=53:47. IR (film): 3379, 2936, 1599, 1501, 1065 cm$^{-1}$. $^1$HNMR and $^{13}$CNMR (DMSO-$d_6$/TMS): cis-isomer, 7.51 (s, 1H, Ar—H), 7.06(m, 2H, Ar—H), 6.94(d, 1H, Ar—H, J=2.0 Hz), 6.75(m, 2H, Ar—H), 6.57(m, 1H, Ar—H), 6.49 (d, 1H, Ar—H, J=3.2 Hz), 5.12(s, 1H, NH), 4.90(d, 10b-H, J=5.6 Hz), 4.43(t, 1H, OH, J=4.8 Hz), 3.20-3.60(m, 5H), 1.84(m, 1H), 1.30-1.70(m, 10H). 147.09, 141.62, 132.78, 129.64, 123.29, 121.88, 120.43, 117.78, 115.18, 114.43, 72.37, 61.43, 60.56, 54.20, 35.27, 33.45, 31.94, 25.76, 22.42, 18.26. trans-isomer, 7.43(s, 1H, Ar—H), 7.06(m, 2H, Ar—H), 6.81(d, 1H, Ar—H, J=2.4 Hz), 6.75(m, 2H, Ar—H), 6.57(m, 1H, Ar—H), 6.51(d, 1H, Ar—H, J=3.2 Hz), 5.40(s, 1H, NH), 4.42(t, 1H, OH, J=4.8 Hz), 4.32(d, 10b-H, J=2.8 Hz), 3.67(m, 1H), 3.20-3.60(m, 4H), 1.75(m, 1H), 1.30-1.70(m, 10H). 147.36, 141.88, 131.61, 129.64, 123.36, 120.36, 119.85, 117.67, 115.08, 114.30, 73.43, 66.19, 61.33, 60.56, 50.07, 35097, 33.28, 33.15, 14.47, 23.43, 21.41. EIMS: m/z 352(M$^+$), 279(100%), 235. HRMS m/z for $C_{22}H_{28}N_2O_2$ Calcd: 352.2151; Found: 352.2145.

Procedure 2:

Via general procedure 2, the titled compound was prepared from 4-(N-phenylamino)-aniline (2 mmol), 2-hydroxy-tetrahydropyran (6 mmol) and indium chloride (0.2-0.4 mmol) in water at room temperature for 24 h. Yield: 89%. Trans/cis=36:64.

Example 3

Synthesis of 2,3,3a,4,5,9b-hexahydro-4-(3-hydroxypropyl)-8-dimethylamino-furano[3,2-c]quinoline (Compound 3-3)

Via the general procedure 1, compound 3-3 was prepared from from 4-(N,N-dimethylamino)-aniline (2 mmol), 3,4-dihydropyran (4 mmol) and indium chloride (0.2-0.4 mmol) in water at room temperature for 5 h. Yield: 46%. Trans/cis=31:69. IR (film): 3329, 2935, 1511, 1451, 1064 cm$^{-1}$. $^1$HNMR and $^{13}$CNMR(DMSO-$d_6$/TMS): cis-isomer, 6.59(s, 1H, Ar—H), 6.51(m, 2H, Ar—H), 4.90(d, 9b-H, J=8.0 Hz), 4.76(s, 1H, NH), 4.49(t, 1H, OH, J=5.2 Hz), 3.58(m, 2H), 3.30(m, 1H), 3.14(m, 1H), 2.67(s, 6H, N—CH$_3$), 2.50(m, 1H), 1.95(m, 1H), 1.30-1.85(m, 5H). 144.21, 138.76, 123.35, 115.98, 115.79, 115.40, 76.15, 66.37, 61.54, 52.95, 42.62, 42.34, 31.05, 29.46, 24.26. trans-isomer, 6.60(s, 1H, Ar—H), 6.51(m, 2H, Ar—H), 5.08(s, 1H, NH), 4.49(t, 1H, OH, J=5.2 Hz), 4.33(d, 9b-H, J=6.0 Hz), 3.74(m, 1H), 3.58(m, 2H), 3.30(m, 2H), 2.68(s, 6H, N—CH$_3$), 2.05(m, 1H), 1.30-1.85(m, 5H). 143.65, 138.76, 121.10, 116.47, 115.98, 115.79, 79.81, 65.42, 61.70, 52.72, 42.62, 41.78, 30.12, 29.59, 29.11. EIMS: m/z 276(M$^+$), 217(100%), 173. HRMS m/z for $C_{16}H_{24}N_2O_2$ Calcd: 276.1838; Found: 276.1832.

Example 4

Synthesis of 6,6a,7,8-tetrahydro-7-(2-o-hydroxyphenyl)ethyl-2H-benzopyrano[3,2-a]quinoline(Compound 4-1)

Via procedure 2, the titled compound was prepared from aniline (2 mmol) and 2-chromanol (6 mmol) and indium chloride (0.2-0.4 mmol) in water at 50° C. for 24 h. Yield: 49%. Cis/trans=24:76. IR (film): 3400, 2926, 1583, 1487, 1227, 753 cm$^{-1}$. $^1$HNMR(CDCl$_3$/TMS): cis-isomer: 6.63-7.38(m, Ar—H, 12H), 5.45(d, 12b-H, J=4.8 Hz), 3.61(m, 7-H, 1H), 2.70-3.03(m, 4H), 2.50(m, 6a-H, 1H), 1.86-2.10 (m, 2H). Trans-isomer: 6.63-7.38(m, Ar—H, 12H), 5.09(d, 12b-H, J=2.8 Hz), 3.42(m, 7-H, 1H), 2.70-3.03(m, 4H), 2.32(m, 6a-H, 1H), 1.86-2.10(m, 2H). EIMS m/z 357(M$^+$), 232(100%). HRMS m/z for $C_{26}H_{27}NO_2$ Calcd: 357.1729; Found: 357.1728.

Example 5

Synthesis of 3,4,4a,5,6,10b-hexahydro-5-(4-hydroxybutyl)-9-hydroxy-2H-pyrano[3,2-c]quinoline (Compound 5-1)

Via the general procedure 1, the titled compound was prepared in 74% yield (trans/cis=26:74): IR (film): 3342, 2936, 1497, 1060 cm$^{-1}$. $^1$HNMR and $^{13}$CNMR(CDCl$_3$/TMS): cis-isomer, 6.94(d, 1H, Ar—H, J=2.8 Hz), 6.61(dd, 1H, Ar—H, J=2.8 Hz, 8.4 Hz), 6.43(d, 1H, Ar—H, J=8.4 Hz), 5.02(d, 10b-H, J=5.2 Hz), 3.69(m, 2H), 3.60(m, 1H), 3.42(m, 1H), 3.25(m, 1H), 2.00(m, 1H), 1.35-1.75(m, 10H). 148.90, 139.01, 121.77, 115.92, 115.84, 113.82, 72.88, 62088, 61.18, 54.70, 35.82, 32.80, 32.31, 25.55, 22.43, 18.01. trans-isomer, 6.71(d, 1H, Ar—H, J=2.8 Hz), 6.61(dd, 1H, Ar—H, J=2.8 Hz, 8.4 Hz), 6.43(d, 1H, Ar—H, J=8.4 Hz), 4.42(d, 10b-H, J=2.8 Hz), 3.90(m, 1H), 3.67(m, 4H), 3.47(m, 1H), 1.91(m, 1H), 1.30-1.80(m, 10H). 147.78, 138.80, 121.57, 117.14, 116.47, 115.96, 73.79, 67.13, 62.97, 50.43, 36.70, 33.06, 32.97, 24.38, 23.09, 21.54. EIMS: m/z 277(M$^+$), 204(100%), 160. HRMS m/z for $C_{16}H_{23}NO_3$ Calcd: 277.1678; Found: 277.1669.

Other Examples

3,4,4a,5,6,10b-hexahydro-5-(4-hydroxybutyl)-2H-pyrano[3,2-c]quinoline

Via the general procedure 1, the titled compound was prepared in 90% yield (trans/cis=32:68). IR (film): 3357, 2935, 1608, 1488, 1066 cm$^{-1}$. $^1$HNMR and —$^{13}$CNMR (CDCl$_3$/TMS): cis-isomer, 7.36(d, 1H, Ar—H, J=7.6 Hz), 7.04(t, 1H, Ar—H, J=7.2 Hz), 6.74(t, 1H, Ar—H, J=7.2 Hz), 6.50(d, 1H, Ar—H, J=6.8 Hz), 5.05(d, 10b-H, J=5.6 Hz), 3.69(t, 2H, J=6.4 Hz), 3.58(m, 1H), 3.40(m, 2H), 2.04(m, 1H), 1.30-1.80(m, 10H). 145.06, 128.19, 127.85, 120.49, 118.21, 114.22, 72.72, 62.44, 60.93, 54.31, 35.66, 32.80, 32.15, 25.66, 22.40, 18.07. trans-isomer, 7.19(d, 1H, Ar—H, J=7.2 Hz), 7.04(t, 1H, Ar—H, J=7.2 Hz), 6.66(t, 1H, Ar—H, J=7.2 Hz), 6.52(d, 1H, Ar—H, J=6.8 Hz), 4.44(d, 10b-H, J=3.2 Hz), 3.92(m, 1H), 3.66(m, 3H), 3.58(m, 1H), 1.93(m, 1H), 1.30-1.80(m, 10H). 144.92, 130.43, 129.25, 120.38, 117.26, 114.49, 74.10, 67.25, 62.50, 49.82, 36.41, 33.06, 32.93, 24.37, 22.99, 21.41. EIMS: m/z 261(M$^+$), 188(100%), 144. Anal. Calcd. For $C_{16}H_{23}NO_2$: C, 73.53; H, 8.87; N, 5.36. Found: C, 73.05; H, 9.17; N, 5.24.

3,4,4a,5,6,10b-hexahydro-5-(4-hydroxybutyl)-9-methyl-2H-pyrano[3,2-c]quinoline Via the general procedure 1, the titled compound was prepared in 88% yield (trans/cis=43:57). IR (film): 3363, 2934, 1621, 1507, 1067 cm$^{-1}$. $^1$HNMR and —$^{13}$CNMR (CDCl$_3$/TMS): cis-isomer, 7.20(d, 1H, Ar—H, J=1.6 Hz), 6.87(dd, 1H, Ar—H, J=1.6 Hz, 8.0 Hz), 6.49(d, 1H, Ar—H, J=8.0 Hz), 5.02(d, 10b-H, J=5.6 Hz), 3.68(t, 2H, J=6.4 Hz), 3.59(m, 1H), 3.40(m, 2H), 2.25(s, 3H, CH$_3$), 2.05(m, 1H), 1.30-1.80(m, 10H). 143.02, 128.88, 127.91, 127.24, 120.23, 114.38, 72.82, 62.45, 61.01, 54.51, 35.87, 32.85, 32.25, 25.69, 22.44, 20.93, 18.09. trans-isomer, 7.03(d, 1H, Ar—H, J=1.6 Hz), 6.98(dd, 1H, Ar—H, J=1.6 Hz, 8.0 Hz), 6.51(d, 1H, Ar—H, J=8.0 Hz), 4.40(d, 10b-H, J=3.2 Hz), 3.94(m, 1H), 3.68(m, 3H), 3.61(m, 1H), 2.21(s, 3H, CH$_3$), 1.95(m, 1H), 1.30-1.80(m, 10H). 142.62, 130.67, 130.01, 126.47, 120.55, 114.72, 74.26, 67.41, 62.50, 49.84, 36.72, 32.97, 32.93, 24.41, 22.95, 21.44, 20.67. EIMS: m/z 275(M$^+$), 202(100%), 158. HRMS m/z for C$_{17}$H$_{25}$NO$_2$ Calcd: 275.1885; Found: 275.1880.

3,4,4a,5,6,10b-hexahydro-5-(4-hydroxybutyl)-9-methoxy-2H-pyrano[3,2-c]quinoline Via the general procedure 1, the titled compound was prepared in 62% yield (trans/cis=34:66): IR (film): 3368, 2934, 1624, 1504, 1065 cm$^{-1}$. $^1$HNMR and —$^{13}$CNMR (CDCl$_3$/TMS): cis-isomer, 6.98(d, 1H, Ar—H, J=2.8 Hz), 6.68(dd, 1H, Ar—H, J=2.8 Hz, 8.4 Hz), 6.50(d, 1H, Ar—H, J=8.4 Hz), 5.02(d, 10b-H, J=5.6 Hz), 3.75(s, 3H, OCH$_3$), 3.68(t, 2H, J=6.4 Hz), 3.60(m, 1H), 3.20-3.40(m, 2H), 2.03(m, 1H), 1.35-1.85(m, 10H). 152.75, 139.38, 121.62, 115.75, 115.08, 112.04, 72.83, 62.45, 61.13, 56.04, 54.03, 35.77, 32.82, 32.25, 25.59, 22.41, 18.03. trans-isomer, 6.80 (d, 1H, Ar—H, J=2.8 Hz), 6.70 (dd, 1H, Ar—H, J=2.8 Hz, 8.4 Hz), 6.52(d, 1H, Ar—H, J=8.4 Hz), 4.43(d, 10b-H, J=3.2 Hz), 3.91(m, 1H), 3.73(s, 3H, OCH$_3$), 3.68(m, 3H), 3.50(m, 1H), 1.94(m, 1H), 1.35-1.85(m, 10H). 151.99, 139.06, 121.29, 116.63, 115.97, 114.39, 74.02, 67.17, 62.51, 56.04, 50.25, 36.67, 32.99, 32.94, 24.35, 23.03, 21.50. EIMS: m/z 291(M$^+$), 218(100%), 174. HRMS m/z for C$_{17}$H$_{25}$NO$_3$ Calcd: 291.1834; Found: 291.1842.

3,4,4a,5,6,10b-hexahydro-5-(4-hydroxybutyl)-9-chloro-2H-pyrano[3,2-c]quinoline Via the general procedure 1, the titled compound was prepared in 51% yield (trans/cis=43:57). IR (film): 3368, 2936, 1605, 1494, 1066 cm$^{-1}$. $^1$HNMR and —$^{13}$CNMR (CDCl$_3$/TMS): cis-isomer, 7.30(d, 1H, Ar—H, J=2.4 Hz), 6.95(dd, 1H, Ar—H, J=2.4 Hz, 8.8 Hz), 6.40(d, 1H, Ar—H, J=8.8 Hz), 4.97(d, 10b-H, J=5.6 Hz), 3.65(t, 2H, J=6.4 Hz), 3.59(m, 1H), 3.38(m, 2H), 2.00(m, 1H), 1.30-1.80(m, 10H). 143.82, 128.10, 127.40, 122.67, 121.93, 115.28, 72.31, 62.72, 61.10, 54.32, 35.33, 32.77, 32.07, 25.52, 22.36, 18.07. trans-isomer, 7.16(d, 1H, Ar—H, J=2.8 Hz), 6.97(dd, 1H, Ar—H, J=2.8 Hz, 8.8 Hz), 6.42(d, 1H, Ar—H, J=8.8 Hz), 4.40(d, 10b-H, J=2.8 Hz), 3.87(m, 1H), 3.65(m, 3H), 3.49(m, 1H), 1.87(m, 1H), 1.30-1.80(m, 10H). 143.35, 129.79, 129.08, 121.67, 121.64, 115.61, 73.29, 67.01, 62.79, 50.27, 36.10, 33.12, 32.77, 24.29, 23.06, 21.46. EIMS: m/z 295(M$^+$), 297(M$^+$+2), 222, 178(100%). HRMS m/z for C$_{16}$H$_{22}$NO$_2$Cl Calcd: 295.1339; Found: 295.1336.

3,4,4a,5,6,10b-hexahydro-5-(4-hydroxybutyl)-9-bromo-2H-pyrano[3,2-c]quinoline Via the general procedure 1, the titled compound was prepared in 36% yield (trans/cis=51:49). IR (film): 3358, 2936, 1696, 1487, 1071 cm$^{-1}$. $^1$HNMR and —$^{13}$CNMR (CDCl$_3$/TMS): cis-isomer, 7.44(d, 1H, Ar—H, J=2.4 Hz), 7.09(dd, 1H, Ar—H, J=2.4 Hz, 8.4 Hz), 6.35(d, 1H, Ar—H, J=8.4 Hz), 4.98(d, 10b-H, J=6.0 Hz), 3.65(t, 2H, J=6.4 Hz), 3.58(m, 1H), 3.35(m, 2H), 2.00(m, 1H), 1.20-1.80(m, 10H). 144.22, 132.69, 130.30, 122.20, 115.70, 109.74, 72.26, 62.81, 61.10, 54.27, 35.29, 32.87, 32.05, 25.51, 22.35, 18.07. trans-isomer, 7.29(d, 1H, Ar—H, J=2.8 Hz), 7.10(dd, 1H, Ar—H, J=2.4 Hz, 8.4 Hz), 6.39(d, 1H, Ar—H, J=8.8 Hz), 4.40(d, 10b-H, J=2.8 Hz), 3.87(m, 1H), 3.65(m, 3H), 3.48(m, 1H), 1.86(m, 1H), 1.20-1.80(m, 10H). 143.74, 131.87, 130.92, 122.42, 116.05, 108.63, 73.22, 67.00, 62.74, 50.26, 36.05, 33.12, 32.77, 24.29, 23.05, 21.45. EIMS: m/z 339(M$^+$), 341(M$^+$+2), 266 (100%), 224. HRMS m/z for C$_{16}$H$_{22}$NO$_2$Br Calcd: 339.0834; Found: 339.0829.

3,4,4a,5,6,10b-hexahydro-5-(4-hydroxybutyl)-9-flouro-2H-pyrano[3,2-c]quinoline Via the general procedure 1, the titled compound was prepared in 68% yield (trans/cis=32:68). IR (film): 3368, 2936, 1497, 1060 cm$^{-1}$. $^1$HNMR and $^{13}$CNMR(CDCl$_3$/TMS): cis-isomer, 7.08(dd, 1H, Ar—H, J=2.8 Hz, 8.8 Hz), 6.75(dt, 1H, Ar—H, J=2.8 Hz, 8.8 Hz), 6.44(dd, 1H, Ar—H, J=4.8 Hz, 8.8 Hz), 5.00(d, 10b-H, J=6.0 Hz), 3.68(t, 2H, J=6.4 Hz), 3.60(m, 1H), 3.34(m, 2H), 2.02(m, 1H), 1.35-1.75(m, 10H). 157.83, 155.49, 141.28, 122.19, 115.18, 114.95, 113.99, 113.77, 72.43, 62.84, 61.15, 54.57, 35.45, 32.80, 32.18, 25.50, 22.39, 18.07. trans-isomer, 6.93(dd, 1H, Ar—H, J=2.8 Hz, 8.8 Hz), 6.78(dt, 1H, Ar—H, J=2.8 Hz, 8.8 Hz), 6.46(dd, 1H, Ar—H, J=4.8 Hz, 8.8 Hz), 4.42(d, 10b-H, J=3.2 Hz), 3.87(m, 1H), 3.68(m, 2H), 3.49(m, 1H), 3.34(m, 1H) 1.90(m, 1H), 1.35-1.85(m, 10H). 156.91, 154.58, 141.03, 121.33, 116.28, 116.05, 115.42, 115.17, 73.37, 67.00, 62.80, 50.44, 36.28, 33.09, 32.90, 24.29, 23.10, 21.51. EIMS: m/z 279(M$^+$), 206(100%), 162. HRMS m/z for C$_{16}$H$_{22}$NO$_2$F Calcd: 279.1635; Found: 279.1632.

3,4,4a,5,6,10b-hexahydro-5-(4-hydroxybutyl)-9-Cyano-2H-pyrano[3,2-c]quinoline Via the general procedure 1, the titled compound was prepared in 30% yield (trans/cis=66:34). IR (film): 3342, 2936, 2212, 1609, 1507, 1062 cm$^{-1}$. $^1$HNMR and —$^{13}$CNMR(CDCl$_3$/TMS): cis-isomer, 7.61(d, 1H, Ar—H, J=2.0 Hz), 7.24(dd, 1H, Ar—H, J=302.0 Hz, 8.8 Hz), 6.43(d, 1H, Ar—H, J=8.8 Hz), 4.97(d, 10b-H, J=5.6 Hz), 4.14(br.s, NH), 3.68(t, 2H, J=6.4 Hz), 3.57(m, 1H), 3.34(m, 2H), 2.00(m, 1H), 1.20-1.80(m, 10H). 148.91, 134.74, 132.26, 121.09, 119.87, 113.64, 98.59, 71.65, 62.43, 60.93, 53.93, 34.70, 32.58, 31.58, 25.45, 22.26, 18.01. trans-isomer, 7.47 (d, 1H, Ar—H, J=1.6 Hz), 7.27(dd, 1H, Ar—H, J=1.6 Hz, 8.4 Hz), 6.47(d, 1H, Ar—H, J=8.4 Hz), 4.52(br.s, NH), 4.44(d, 10b-H, J=2.8 Hz), 3.85(m, 1H), 3.68(m, 3H), 3.44 (m, 1H), 1.80(m, 1H), 1.20-1.(m, 10H). 148.43, 132.26, 120.96, 119.87, 114.13, 97.65, 72.76, 66.86, 62.37, 50.26, 35.33, 33.00, 32.63, 24.11, 22.93, 21.30. EIMS: m/z 286 (M$^+$), 213(100%), 169. HRMS m/z for C$_{17}$H$_{22}$N$_2$O$_2$ Calcd: 286.1681; Found: 286.1682.

2,3,3a,4,5,9b-hexahydro-4-(3-hydroxypropyl)-furano[3,2-c]quinoline

Via the general procedure 1, the titled compound was prepared in 85% yield (trans/cis=22:78). IR (film): 3336, 2932, 1608, 1497, 1061 cm$^{-1}$. $^1$HNMR and —$^{13}$CNMR (CDCl$_3$/TMS): cis-isomer, 7.29(d, 1H, Ar—H, J=7.6 Hz), 7.04(m, 1H, Ar—H), 6.76(m, 1H, Ar—H), 6.30(d, 1H, Ar—H, J=8.0 Hz), 5.11(d, 9b-H, J=8.0 Hz), 3.79(m, 2H), 3.70(m, 2H), 3.44(m, 1H), 2.63(m, 1H), 2.64(br.s, OH), 2.03(m, 1H), 1.55-1.90(m, 5H). 145.24, 130.25, 128.55, 122.84, 118.94, 114.86, 76.02, 66.81, 62.52, 52.68, 42.69, 30.93, 29.21, 24.22. trans-isomer, 7.34(d, 1H, Ar—H, J=7.6 Hz), 7.09(m, 1H, Ar—H), 6.76(m, 1H, Ar—H), 6.64(d, 1H, Ar—H, J=8.0 Hz), 4.56(d, 9b-H, J=5.6 Hz), 3.95(m, 1H), 3.79(m, 2H), 3.70(m, 2H), 2.82(m, 1H), 2.64(br.s, 1H, OH), 2.20(m, 1H), 1.55-1.90(m, 5H). 145.16, 131.20, 129.10, 120.48, 118.42, 115.08, 76.10, 65.76, 62.64, 52.16, 41.39, 30.09, 29.37, 28.79. EIMS: m/z 233(M$^+$), 174(100%), 130. HRMS m/z for $C_{14}H_{19}NO_2$ Calcd: 233.1416; Found: 233.1414.

2,3,3a,4,5,9b-hexahydro-4-(3-hydroxypropyl)-8-methyl-furano[3,2-c]quinoline

Via the general procedure 1, the titled compound was prepared in 84% yield (trans/cis=19:81). IR (film): 3342, 2920, 1618, 1507, 1061 cm$^{-1}$. $^1$HNMR and —$^{13}$CNMR (CDCl$_3$/TMS): cis-isomer, 7.11(d, 1H, Ar—H, J=2.0 Hz), 6.86(dd, 1H, Ar—H, J=2.0 Hz, 8.0 Hz), 6.46(d, 1H, Ar—H, J=8.0 Hz), 5.08(d, 9b-H, J=8.0 Hz), 3.80(m, 2H), 3.70(m, 2H), 3.40(m, 1H), 2.85(br.s, OH), 2.62(m, 1H), 2.23(s, 3H, CH$_3$), 2.04(m, 1H), 1.55-1.90(m, 5H). 142.94, 130.51, 129.32, 128.17, 122.87, 115.00, 76.14, 66.89, 62.50, 53.00, 42.80, 30.97, 29.28, 24.28, 20.80. trans-isomer, 7.17(d, 1H, Ar—H, J=2.0 Hz), 6.91(dd, 1H, Ar—H, J=2.0 Hz, 8.0 Hz), 6.58(d, 1H, Ar—H, J=8.0 Hz), 4.54(d, 9b-H, J=5.2 Hz), 3.95(m, 1H), 3.80(m, 2H), 3.70(m, 2H), 2.85(br.s, 1H, OH), 2.79(m, 1H), 2.24(s, 3H, CH$_3$), 2.20(m, 1H), 1.55-1.90(m, 5H). 142.77, 131.33, 129.81, 127.74, 120.74, 115.24, 76.14, 65.87, 62.65, 52.55, 41.65, 30.17, 29.45, 28.86, 20.73. EIMS: m/z 247(M$^{-+}$), 188(100%), 144. Anal. Calcd. For $C_{15}H_{21}NO_2$: C, 72.84; H, 8.56; N, 5.66. Found: C, 73.37; H, 8.90; N, 5.66.

2,3,3a,4,5,9b-hexahydro-4-(3-hydroxypropyl)-8-methoxy-furano[3,2-c]quinoline Via the general procedure 1, the titled compound was prepared in 81% yield (trans/cis=13:87). IR (film): 3333, 2932, 1505, 1059 cm$^{-1}$. $^1$HNMR and $^{13}$CNMR(CDCl$_3$/TMS): cis-isomer, 6.86(d, 1H, Ar—H, J=2.8 Hz), 6.68(dd, 1H, Ar—H, J=2.8 Hz, 8.4 Hz), 6.52(d, 1H, Ar—H, J=8.8 Hz), 5.07(d, 9b-H, J=8.0 Hz), 3.79(m, 2H), 3.75(s, 3H, OCH$_3$), 3.71(m, 2H), 3.38(m, 1H), 2.84(br.s, OH), 2.62(m, 1H), 2.03(m, 1H), 1.55-1.90(m, 5H). 152.90, 139.31, 123.72, 116.18, 115.76, 114.05, 76.24, 66.90, 62.43, 55.90, 53.09, 42.67, 30.97, 29.25, 24.10. trans-isomer, 6.93(d, 1H, Ar—H, J=2.8 Hz), 6.73(dd, 1H, Ar—H, J=2.8 Hz, 8.8 Hz), 6.65(d, 1H, Ar—H, J=8.8 Hz), 4.56(d, 9b-H, J=5.6 Hz), 3.96(m, 1H), 3.79(m, 2H), 3.75(s, 3H, OCH$_3$), 3.71(m, 2H), 2.84(br.s, 1H, OH), 2.77(m, 1H), 2.23(m, 1H), 1.55-1.90(m, 5H). 152.62, 139.20, 121.72, 116.51, 116.46, 114.73, 76.24, 65.96, 62.57, 55.97, 52.94, 41.73, 30.16, 29.44, 28.84. EIMS: m/z 263(M$^+$), 204(100%), 160. Anal. Calcd. For $C_{15}H_{21}NO_3$: C, 68.42; H, 8.04; N, 5.32. Found: C, 68.61; H, 8.40; N, 4.96.

2,3,3a,4,5,9b-hexahydro-4-(3-hydroxypropyl)-8-chloro-furano[3,2-c]quinoline

Via the general procedure 1, the titled compound was prepared in 77% yield (trans/cis=26:74). IR (film): 3343, 2936, 1605, 1492, 1062 cm$^{-1}$. $^1$HNMR and —$^{13}$CNMR (CDCl$_3$/TMS): cis-isomer, 7.25(d, 1H, Ar—H, J=2.4 Hz), 6.96(dd, 1H, Ar—H, J=2.4 Hz, 8.4 Hz), 6.44(d, 1H, Ar—H, J=8.4 Hz), 5.03(d, 9b-H, J=8.0 Hz), 3.79(m, 2H), 3.70(m, 2H), 3.42(m, 1H), 2.90(br.s, OH), 2.59(m, 1H), 1.97(m, 1H), 1.55-1.90(m, 5H). 143.78, 129.66, 128.39, 124.09, 122.86, 116.02, 75.56, 66.91, 62.39, 52.37, 42.29, 30.88, 29.10, 24.01. trans-isomer, 7.30(d, 1H, Ar—H, J=2.4 Hz), 7.02(dd, 1H, Ar—H, J=2.4 Hz, 8.4 Hz), 6.55(d, 1H, Ar—H, J=8.4 Hz), 4.50(d, 9b-H, J=5.6 Hz), 3.93(m, 1H), 3.79(m, 2H), 3.70(m, 2H), 2.90(br.s, 1H, OH), 2.79(m, 1H), 2.19(m, 1H), 1.55-1.90(m, 5H). 143.85, 130.59, 128.92, 122.26, 121.78, 116.22, 75.56, 65.80, 62.49, 52.17, 41.13, 30.03, 29.27, 28.72. EIMS: m/z 269(M$^+$+2), 267(M$^+$), 208(100%), 164. HRMS m/z for $C_{14}H_{18}NO_2Cl$ Calcd: 267.1026; Found: 267.1026.

2,3,3a,4,5,9b-hexahydro-4-(3-hydroxypropyl)-8-bromo-furano[3,2-c]quinoline

Via the general procedure 1, the titled compound was prepared in 81% yield (trans/cis=13:87). IR (film): 3343, 2936, 1598, 1488, 1062 cm$^{-1}$. $^1$HNMR and —$^{13}$CNMR (CDCl$_3$/TMS): cis-isomer, 7.40(d, 1H, Ar—H, J=2.4 Hz), 7.11(dd, 1H, Ar—H, J=2.4 Hz, 8.8 Hz), 6.42(d, 1H, Ar—H, J=8.8 Hz), 5.04(d, 9b-H, J=7.6 Hz), 3.80(m, 2H), 3.72(m, 2H), 3.44(m, 1H), 2.61(m, 1H), 1.98(m, 1H), 1.55-1.90(m, 5H). 144.10, 132.66, 131.21, 124.75, 116.36, 110.20, 75.50, 66.90, 62.58, 52.33, 42.38, 30.97, 29.17, 24.03. trans-isomer, 7.47(d, 1H, Ar—H, J=2.4 Hz), 7.18(dd, 1H, Ar—H, J=2.4 Hz, 8.8 Hz), 6.58(d, 1H, Ar—H, J=8.8 Hz), 4.53(d, 9b-H, J=5.6 Hz), 3.95(m, 1H), 3.80(m, 2H), 3.72(m, 2H), 2.81(m, 1H), 2.21(m, 1H), 1.55-1.90(m, 5H). 144.18, 133.54, 131.72, 122.45, 116.60, 109.57, 75.44, 65.84, 62.68, 52.19, 41.26, 30.13, 29.33, 28.81. EIMS: m/z 313(M$^+$+2), 311(M$^+$), 252(100%), 210. HRMS m/z for $C_{14}H_{18}NO_2Br$ Calcd: 311.0521; Found: 311.0528.

2,3,3a,4,5,9b-hexahydro-4-(3-hydroxypropyl)-8-fluoro-furano[3,2-c]quinoline

Via the general procedure 1, the titled compound was prepared in 85% yield (trans/cis=14:86). IR (film): 3342, 2936, 1501, 1061 cm$^{-1}$. $^1$HNMR and $^{13}$CNMR(CDCl$_3$/TMS): cis-isomer, 7.00(dd, 1H, Ar—H, J=2.8 Hz, 8.8 Hz), 6.75(dt, 1H, Ar—H, J=2.8 Hz, 8.8 Hz), 6.46(dd, 1H, Ar—H, J=4.8 Hz, 8.8 Hz), 5.05(d, 9b-H, J=8.0 Hz), 3.79(m, 2H), 3.71(m, 2H), 3.41(m, 1H), 2.60(m, 1H), 2.00(m, 1H), 1.55-1.90(m, 5H). 157.71, 155.36, 141.33, 124.12, 116.04, 115.82, 115.60, 115.37, 75.81, 66.93, 62.70, 52.83, 42.49, 31.03, 29.23, 24.01. trans-isomer, 7.06(dd, 1H, Ar—H, J=2.8 Hz, 8.8 Hz), 6.82(dt, 1H, Ar—H, J=2.8 Hz, 8.8 Hz), 6.59(dd, 1H, Ar—H, J=4.8 Hz, 8.8 Hz), 4.52(d, 9b-H, J=5.6 Hz), 3.95(m, 1H), 3.79(m, 2H), 3.71(m, 2H), 2.77(m, 1H), 2.21(m, 1H), 1.55-1.90(m, 5H). 157.26, 154.91, 141.46, 121.85, 116.85, 116.63, 116.13, 115.88, 75.68, 65.99, 62.81, 52.77, 41.53, 30.19, 29.40, 28.85. EIMS: m/z 251(M$^+$), 192(100%), 148. HRMS m/z for $C_{14}H_{18}NO_2F$ Calcd: 251.1322; Found: 251.1316.

2,3,3a,4,5,9b-hexahydro-4-(3-hydroxypropyl)-8-hydroxy-furano[3,2-c]quinoline Via the general procedure 1, the titled compound was prepared in 73% yield (trans/cis=4:96). IR (film): 3342, 2936, 1502, 1059 cm$^{-1}$. $^1$HNMR and $^{13}$CNMR(DMSO-d$_6$/TMS): cis-isomer, 8.47(s, 1H, Ar—OH), 6.50(d, 1H, Ar—H, J=2.4 Hz), 6.40(s, 1H, Ar—H), 6.39(d, 1H, Ar—H, J=2.8 Hz), 4.85(d, 9b-H, J=8.0 Hz), 4.73(br.s, 1H, NH), 4.50(t, 1H, OH, J=4.8 Hz), 3.56(m, 2H), 3.40(m, 2H), 3.13(m, 1H), 2.45(m, 1H), 1.40-1.85(m, 5H). 149.52, 139.24, 123.76, 116.05, 116.03, 75.94, 66.35, 61.54, 52.94, 42.44, 31.05, 29.41, 24.17. trans-isomer, 8.49(s, 1H, Ar—OH), 6.50(d, 1H, Ar—H, J=2.4 Hz), 6.43(s, 1H, Ar—H),), 6.37(d, 1H, Ar—H, J=2.8 Hz), 5.04(br.s, 1H, NH), 4.29(d, 9b-H, J=6.0 Hz), 4.50(t, 1H, OH, J=4.8 Hz), 3.72(m, 1H), 3.56(m, 2H), 3.40(m, 2H), 2.45(m, 1H), 1.40-1.85(m, 5H). 148.94, 121.61, 116.88, 116.53, 76.81, 65.46, 61.70, 52.81, 41.74, 30.13, 29.41, 29.08. EIMS: m/z 249(M+), 190(100%), 146. HRMS m/z for $C_{14}H_{19}NO_3$ Calcd: 249.1365; Found: 249.1355.

2,3,3a,4,5,9b-hexahydro-4-(3-hydroxypropyl)-8-cyano-furano[3,2-c]quinoline

Via the general procedure 1, the titled compound was prepared in 38% yield (trans/cis=23:77). IR (liquid film): 3350, 2942, 2212, 1608, 1515, 1060 cm$^{-1}$. $^1$HNMR and —$^{13}$CNMR(CDCl$_3$/TMS): cis-isomer, 7.44(d, 1H, Ar—H, J=2.0 Hz), 7.13(dd, 1H, Ar—H, J=2.0 Hz, 8.4 Hz), 6.43(d, 1H, Ar—H, J=8.4 Hz), 4.94(d, 9b-H, J=7.6 Hz), 4.83(br.s, 1H, NH), 3.73(m, 2H), 3.61(m, 2H), 3.47(m, 1H), 3.06(br.s, 1H, OH), 2.52(m, 1H), 1.40-2.20(m, 6H). 148.53, 134.58, 132.20, 122.36, 120.82, 114.45, 98.98, 74.71, 66.83, 62.24, 51.38, 41.83, 30.90, 29.05, 23.97. trans-isomer, 7.46(d, 1H, Ar—H, J=2.0 Hz), 7.18(dd, 1H, Ar—H, J=2.0 Hz, 8.4 Hz), 6.53(d, 1H, Ar—H, J=8.4 Hz), 5.37(br.s, 1H, NH), 4.41(d, 9b-H, J=5.2 Hz), 3.84(m, 1H), 3.73(m, 2H), 3.61(m, 2H), 3.30(br.s, 1H, OH), 2.81(m, 1H), 1.40-2.20(m, 6H). 148.88, 135.82, 132.75, 122.36, 119.59, 114.74, 98.09, 74.94, 65.61, 62.33, 51.45, 40.29, 30.13, 29.17, 28.68. EIMS: m/z 258 (M+), 199(100%), 155. HRMS m/z for $C_{15}H_{18}N_2O_2$ Calcd: 258.1368; Found: 258.1362.

3,4,4a,5,6,12b-hexahydro-5-(4-hydroxybutyl)-benzo[h]-2H-pyrano[3,2-c]quinoline

Via the general procedure 1, the titled compound was prepared in 65% yield (trans/cis=70:30). IR (film): 3340, 2936, 1574, 1524, 1078 cm$^{-1}$. $^1$HNMR and —$^{13}$CNMR (CDCl$_3$/TMS): cis-isomer, 7.76(m, 2H, Ar—H), 7.54(d, 1H, Ar—H, J=8.4 Hz), 7.42(m, 2H, Ar—H), 7.31(d, 1H, Ar—H, J=8.4 Hz), 5.21(d, 10b-H, J=6.0 Hz), 3.72(m, 2H), 3.61(m, 1H), 3.50(m, 1H), 3.32(m, 1H), 2.15(m, 1H), 1.35-1.85(m, 10H). 140.14, 133.86, 128.78, 125.88, 125.54, 125.05, 122.91, 120.37, 117.98, 114.65, 72.85, 61.14, 54.54, 34.89, 32.83, 32.12, 25.54, 22.46, 18.06. trans-isomer, 7.76(m, 2H, Ar—H), 7.35(d, 1H, Ar—H, J=8.4 Hz), 7.42(m, 2H, Ar—H), 7.22(d, 1H, Ar—H, J=8.4 Hz), 4.59(d, 10b-H, J=2.8 Hz), 3.91(m, 1H), 3.72(m, 4H), 1.95(m, 1H), 1.30-1.85(m, 10H). 139.90, 134.47, 128.81, 128.19, 126.12, 124.91, 123.01, 120.37, 117.18, 114.61, 74.23, 67.19, 62.60, 50.41, 36.14, 33.03, 32.92, 24.33, 23.14, 21.57. EIMS: m/z 311(M+), 238 (100%). HRMS m/z for $C_{20}H_{25}NO_2$ Calcd: 311.1885; Found: 311.1888.

3,4,4a,5,6,12b-hexahydro-5-(4-hydroxybutyl)-benzo[h]furano[3,2-c]quinoline

Via the general procedure 1, the titled compound was prepared in 81% yield (trans/cis=32:68). IR (film): 3347, 2936, 1703, 1575, 1524, 1058 cm$^{-1}$. $^1$HNMR and —$^{13}$CNMR(CDCl$_3$/TMS): cis-isomer, 7.75(m, 2H, Ar—H), 7.43(m, 3H, Ar—H), 5.30(d, 10b-H, J=7.6 Hz), 3.77(m, 4H), 3.55(m, 1H), 2.70(m, 1H), 2.25(m, 1H), 1.70-1.95(m, 5H). 139.98, 133.92, 128.82, 127.74, 126.09, 125.24, 122.98, 120.48, 118.46, 116.61, 76.67, 69.46, 62.62, 52.71, 42.43, 31.28, 29.47, 24.08. trans-isomer, 7.81(m, 2H, Ar—H), 7.43(m, 4H, Ar—H), 4.68(d, 10b-H, J=5.2 Hz), 4.01(m, 1H), 3.77(m, 4H), 2.91(m, 1H), 2.08(m, 1H), 1.70-1.95(m, 5H). 140.40, 134.29, 128.75, 127.74, 126.25, 125.14, 123.26, 120.66, 117.77, 114.21, 76.73, 65.71, 62.70, 52.54, 40.98, 30.18, 29.39, 29.23. HRMS m/z for $C_{18}H_{21}NO_2$ Calcd: 283.1572; Found: 283.1575.

3,4,4a,5,6,10b-hexahydro-5-(4-hydroxybutyl)-6-methyl-2H-pyrano[3,2-c]quinoline

Via the general procedure 1, the titled compound was prepared in 60% yield (trans/cis=40:60). IR (film): 3395, 2934, 1602, 1490, 1062 cm$^{-1}$. $^1$HNMR and —$^{13}$CNMR (CDCl$_3$/TMS): cis-isomer, 7.40(d, 1H, Ar—H, J=7.6 Hz), 7.16(t, 1H, Ar—H, J=7.2 Hz), 6.74(t, 1H, Ar—H, J=7.2 Hz), 6.48(d, 1H, Ar—H, J=8.4 Hz), 4.95(d, 10b-H, J=6.0 Hz), 3.64(m, 4H), 3.43(m, 1H), 2.95(s, 3H, N—CH$_3$), 2.09(m, 1H), 1.30-1.95(m, 10H). 147.54, 128.60, 128.06, 121.68, 117.18, 113.23, 69.26, 62.74, 62.35, 61.43, 37.26, 35.59, 33.22, 30.68, 25.21, 23.48, 19.68. trans-isomer, 7.35(d, 1H, Ar—H, J=7.6 Hz), 7.16(t, 1H, Ar—H, J=7.2 Hz), 6.68(t, 1H, Ar—H, J=7.2 Hz), 6.70(d, 1H, Ar—H, J=7.2 Hz), 4.88(d, 10b-H, J=5.2 Hz), 3.64(m, 4H), 3.13(m, 1H), 2.90(s, 3H, N—CH$_3$), 2.19(m, 1H), 1.30-1.95(m, 10H). 144.76, 128.66, 127.57, 118.85, 115.86, 110.68, 72.86, 65.71, 62.69, 61.06, 38.88, 33.65, 33.02, 31.28, 25.98, 24.89, 22.62.

EIMS: m/z 275(M+), 202(100%), 158. HRMS m/z for $C_{17}H_{25}NO_2$ Calcd: 275.1885; Found: 275.1886.

3,4,4a,5,6,10b-hexahydro-5-(4-hydroxybutyl)-6-ethyl-2H-pyrano[3,2-c]quinoline

Via the general procedure 1, the titled compound was prepared in 35% yield (trans/cis=15:85). IR (film): 3374, 2936, 1604, 1495, 1033 cm$^{-1}$. $^1$HNMR and —$^{13}$CNMR (CDCl$_3$/TMS): cis-isomer, 7.39(d, 1H, Ar—H, J=7.6 Hz), 7.13(t, 1H, Ar—H, J=8.0 Hz), 6.64(t, 1H, Ar—H, J=7.4 Hz), 6.51(d, 1H, Ar—H, J=8.4 Hz), 4.95(d, 10b-H, J=6.0 Hz), 3.68(t, 2H, J=7.4 Hz), 3.50(m, 3H), 2.25(q, 2H, N—CH$_2$), 2.15(m, 1H), 1.30-1.95(m, 10H), 1.14(t, 3H, J=6.8 Hz). 143.32, 128.50, 127.93, 118.24, 115.10, 110.18, 68.96, 63.30, 62.89, 60.79, 44.32, 33.02, 32.93, 32.55, 26.09, 24.87, 22.58, 12.65. trans-isomer, 7.35(d, 1H, Ar—H, J=8.0 Hz), 7.16(t, 1H, Ar—H, J=8.0 Hz), 6.71(t, 1H, Ar—H, J=5.2 Hz), 6.69(d, 1H, Ar—H, J=8.4 Hz), 4.90(d, 10b-H, J=5.2 Hz), 3.68(t, 2H, J=7.4 Hz), 3.50(m, 3H), 3.25(q, 2H, N—CH$_2$), 2.15(m, 1H), 1.30-1.95(m, 10H), 1.09(t, 3H, J=6.8 Hz). 146.45, 128.50, 128.08, 121.55, 116.79, 112.79, 72.74, 62.90, 61.80, 58.93, 42.40, 34.89, 33.22, 30.22, 25.38, 23.05, 19.10, 12.94. EIMS: m/z 289(M+), 216(100%), 172. HRMS m/z for $C_{18}H_{27}NO_2$ Calcd: 289.2042; Found: 289.2038.

3,4,4a,5,6,10b-hexahydro-5-(4-hydroxybutyl)-6-butyl-2H-pyrano[3,2-c]quinoline

Via the general procedure 1, the titled compound was prepared in 34% yield (trans/cis=16:84). IR (film): 3374, 2936, 1602, 1487, 1073 cm$^{-1}$. $^1$HNMR and —$^{13}$CNMR (CDCl$_3$/TMS): cis-isomer, 7.39(d, 1H, Ar—H, J=7.2 Hz), 7.12(t, 1H, Ar—H, J=7.6 Hz), 6.69(t, 1H, Ar—H, J=7.6 Hz), 6.34(d, 1H, Ar—H, J=8.0 Hz), 4.95(d, 9b-H, J=8.0 Hz), 4.01(m, 1H), 3.67(t, 2H, J=6.8 Hz), 3.54(m, 2H), 3.89(m, 1H), 2.90(m, 1H), 2.08(m, 1H), 1.25-1.90(m, 14H), 0.96(t, 3H, J=7.2 Hz). 143.68, 129.35, 127.88, 118.25, 115.16, 110.25, 68.86, 63.84, 62.31, 60.76, 50.02, 34.99, 33.00, 32.07, 30.93, 29.71, 25.67, 24.92, 22.52, 19.56. trans-isomer, 7.33(d, 1H, Ar—H, J=7.6 Hz), 7.12(t, 1H, Ar—H, J=7.6 Hz), 6.69(t, 1H, Ar—H, J=7.6 Hz), 6.48(d, 1H, Ar—H, J=6.4 Hz), 4.88(s, 1H, NH), 4.85(d, 9b-H, J=5.6 Hz), 4.01(m, 1H), 3.67(t, 2H, J=6.8 Hz), 3.59(m, 2H), 3.39(m, 1H), 3.23(m, 1H), 3.09(m, 1H), 2.16(m, 1H), 1.25-1.90(m, 14H), 0.94(t, 3H, J=7.2 Hz). 146.41, 128.52, 128.34, 121.42, 116.60, 112.73, 72.85, 64.11, 62.92, 59.79, 48.65, 34.99, 33.22, 32.18, 30.40, 29.86, 25.47, 23.19, 20.54, 14.24. EIMS: m/z 317(M$^+$), 244(100%), 200. HRMS m/z for $C_{20}H_{31}NO_2$ Calcd: 317.2355; Found: 317.2341.

2,3,3a, 4,5,9b-hexahydro-4-(3-hydroxypropyl)-5-methyl-furano[3,2-c]quinoline Via the general procedure 1, the titled compound was prepared in 65% yield (trans/cis=45:55). IR (film): 3394, 2936, 1604, 1498, 1040 cm$^{-1}$. $^1$HNMR and —$^{13}$CNMR (CDCl$_3$/TMS): cis-isomer, 7.25(d, 1H, Ar—H, J=7.2 Hz), 7.12(t, 1H, Ar—H, J=7.2 Hz), 6.68(t, 1H, Ar—H, J=7.2 Hz), 6.48(d, 1H, Ar—H, J=8.4 Hz), 4.99(d, 9b-H, J=8.0 Hz), 3.76(m, 2H), 3.49(m, 2H), 3.14(m, 1H), 2.90(s, 3H, N—CH$_3$), 2.70(m, 1H), 1.40-2.20(m, 6H). 144.58, 129.89, 129.06, 122.69, 117.03, 111.46, 73.78, 66.31, 62.69, 62.55, 41.16, 38.83, 29.91, 29.90, 27.52. trans-isomer, 7.31(d, 1H, Ar—H, J=7.6 Hz), 7.17(t, 1H, Ar—H, J=7.2 Hz), 6.73(t, 1H, Ar—H, J=7.2 Hz), 6.64(d, 1H, Ar—H, J=8.0 Hz), 4.63(d, 9b-H, J=6.4 Hz), 3.76(m, 2H), 3.49(m, 2H), 3.14(m, 1H), 2.95(s, 3H, N—CH$_3$), 2.63(m, 1H), 1.40-2.20(m, 6H). 145.71, 130.56, 129.20, 122.63, 117.43, 112.91, 75.87, 66.01, 62.82, 60.72, 40.91, 38.83, 31.29, 27.72, 26.02. EIMS: m/z 247(M$^+$), 188(100%), 144. HRMS m/z for $C_{15}H_{21}NO_2$ Calcd: 247.1572; Found: 247.1569.

2,3,3a,4,5,9b-hexahydro-4-(3-hydroxypropyl)-5-ethyl-furano[3,2-c]quinoline

Via the general procedure 1, the titled compound was prepared in 32% yield (trans/cis=17:83). IR (film): 3400, 2929, 1605, 1495, 1036 cm$^{-1}$. $^1$HNMR and —$^{13}$CNMR (CDCl$_3$/TMS): cis-isomer, 7.27(d, 1H, Ar—H, J=7.2 Hz), 7.11(t, 1H, Ar—H, J=7.2 Hz), 6.65(t, 1H, Ar—H, J=7.2 Hz), 6.54(d, 1H, Ar—H, J=8.4 Hz), 5.00(d, 9b-H, J=7.6 Hz), 3.55(m, 3H), 3.24(m, 2H), 2.60(m, 1H), 1.40-2.20(m, 6H). 143.08, 130.23, 128.91, 122.35, 116.33, 111.03, 73.70, 66.25, 62.88, 59.98, 44.75, 40.91, 29.87, 29.69, 29.04, 13.28. trans-isomer, 7.35(d, 1H, Ar—H, J=7.2 Hz), 7.16(t, 1H, Ar—H, J=7.2 Hz), 6.75(d, 1H, Ar—H, J=7.2 Hz), 6.73(t, 1H, Ar—H, J=7.2 Hz), 4.64(d, 9b-H, J=6.4 Hz), 3.81(t, 2H, J=7.6 Hz), 3.55(m, 3H), 3.24(m, 2H), 2.59(m, 1H), 1.40-2.20(m, 6H). 144.16, 130.75, 129.00, 122.98, 117.23, 113.90, 75.74, 65.84, 63.05, 58.37, 45.34, 40.60, 30.87, 27.65, 25.79, 13.60. EIMS: m/z 261(M$^+$), 202(100%), 158. HRMS m/z for $C_{16}H_{23}NO_2$ Calcd: 261.1729; Found: 261.1720.

2,3,3a, 4,5,9b-hexahydro-4-(3-hydroxypropyl)-5-butyl-furano[3,2-c]quinoline

Via the general procedure 1, the titled compound was prepared in 34% yield (trans/cis=15:85). IR (film): 3394, 2955, 1605, 1495, 1039 cm$^{-1}$. $^1$HNMR and —$^{13}$CNMR (CDCl$_3$/TMS): cis-isomer, 7.26(d, 1H, Ar—H, J=7.2 Hz), 7.11(t, 1H, Ar—H, J=7.6 Hz), 6.65(t, 1H, Ar—H, J=7.6 Hz), 6.51(d, 1H, Ar—H, J=8.0 Hz), 5.01(d, 9b-H, J=8.0 Hz), 3.82(m, 2H), 3.56(m, 3H), 3.20(m, 1H), 2.92(m, 1H), 2.64(m, 1H), 1.30-2.30(m, 10H). 143.34, 130.21, 128.86, 122.35, 116.31, 111.03, 73.62, 67.53, 62.88, 59.60, 50.57, 40.93, 33.46, 30.26, 28.75, 25.55, 23.65, 14.28. trans-isomer, 7.34(d, 1H, Ar—H, J=7.6 Hz), 7.16(t, 1H, Ar—H, J=7.6 Hz), 6.72(t, 1H, Ar—H, J=7.6 Hz), 6.72(d, 1H, Ar—H, J=6.4 Hz), 4.57(d, 9b-H, J=6.0 Hz), 3.82(m, 2H), 3.56(m, 3H), 2.24(m, 1H), 3.06(m, 1H), 2.60(m, 1H), 1.30-2.30(m, 6H), 0.92(t, 3H, J=7.2 Hz). 143.88, 130.86, 129.00, 122.56, 116.89, 113.58, 75.83, 65.75, 63.06, 59.77, 51.71, 40.42, 31.05, 30.40, 28.17, 25.31, 20.62, 14.21. EIMS: m/z 289(M$^+$), 230(100%), 186. HRMS m/z for $C_{18}H_{27}NO_2$ Calcd: 289.2042; Found: 289.2040.

2,3,3 a,4,5,9b-hexahydro-4-(3-hydroxybutyl)furano[3,2-a]quinoline

Via the general procedure 2, the titled compound was prepared in 86% yield (trans/cis=46:54). IR (film): 3349, 2935, 1610, 1497, 1060 cm$^{-1}$. $^1$HNMR (CDCl$_3$/TMS): cis-isomer, 7.28(d, 1H, Ar—H, J=7.6 Hz), 7.03(t, 1H, Ar—H, J=8.0 Hz), 6.75(t, 1H, Ar—H, J=8.0 Hz), 6.50(d, 1H, Ar—H, J=8.0 Hz), 5.11(d, 9b-H, J=8.0 Hz), 3.79(m, 2H), 3.71(m, 2H), 3.44(m, 1H), 2.62(m, 1H), 2.64(br.s, OH), 2.03(m, 1H), 1.55-1.90(m, 5H). trans-isomer, 7.33(d, 1H, Ar—H, J=7.6 Hz), 7.09(t, 1H, Ar—H, J=7.6 Hz), 6.75(t, 1H, Ar—H, J=7.6 Hz), 6.62(d, 1H, Ar—H, J=8.0 Hz), 4.55(d, 9b-H, J=5.2 Hz), 3.95(m, 1H), 3.79(m, 2H), 3.70(m, 2H), 2.82(m, 1H), 2.64(br.s, 1H, OH), 2.20(m, 1H), 1.55-1.90(m, 5H). EIMS m/z 233(M$^+$), 174(100%), 130. HRMS m/z for $C_{14}H_{19}NO_2$ Calcd: 233.1416; Found: 233.1416.

2,3,3a,4,5,9b-hexahydro-2-methyl-4-(3-hydroxybutyl)furano[3,2-a]quinoline

Via the general procedure 2, the titled compound was prepared in 88% yield (trans/cis=48:52). IR (film): 3370, 2963, 1615, 1489, 1075 cm. $^1$HNMR(CDCl$_3$/TMS): 7.31(m, Ar—H, 1H), 7.05(m, Ar—H, 1H), 6.73(m, Ar—H, 1H), 6.60 and 6.50(m, Ar—H, 1H), 5.16(d, 9b-H, J=8.0 Hz), 5.05(d, 9b-H, J=8.4 Hz), 4.83(d, 9b-H, J=6.0 Hz), 4.53(d, 9b-H, J=5.6 Hz), 3.95-4.20(m, 1H), 3.84(m, 1H), 3.39 and 3.32(m, 1H), 2.93 and 2.72(m, 1H), 1.40-2.40(m, 6H), 1.10-1.35(m, 6H, CH$_3$). EIMS m/z 261(M$^+$), 188(100%), 130. HRMS m/z for $C_{16}H_{23}NO_2$ Calcd: 261.1729; Found: 261.1717.

2,3,3a,4,5,9b-hexahydro-2-ethyl-4-(3-hydroxypentyl)furano[3,2-a]quinoline

Via the general procedure 2, the titled compound was prepared in 81% yield (trans/cis=48:52). IR (film): 3365, 2932, 1610, 1494, 1032 cm$^{-1}$ $^1$HNMR(CDCl$_3$/TMS): 7.30 (m, Ar—H, 1H), 7.04(m, Ar—H, 1H), 6.73(m, Ar—H, 1H), 6.60(m, Ar—H, 1H), 5.14(d, 9b-H, J=8.0 Hz), 5.06(d, 9b-H, J=8.4 Hz), 4.76(d, 9b-H, J=5.2 Hz), 4.53(d, 9b-H, J=6.0 Hz), 3.94, 3.82 and 3.74(m, 1H), 3.57, 3.41 and 3.36 (m, 1H), 2.94, 2.76 and 2.66(m, 1H), 1.20-2.30(m, 11H), 0.96, 0.64, 0.88 and 0.80(t, 6H, J=7.6 Hz, CH$_3$). EIMS m/z 289(M$^+$), 202(100%), 130. HRMS m/z for $C_{18}H_{27}NO_2$ Calcd: 289.2042; Found: 289.2033.

2,3,3a,4,5,9b-hexahydro-2-heptyl-4-(3-hydroxydecyl)furano[3,2-a]quinoline

Via the general procedure 2, the titled compound was prepared in 41% yield (trans/cis=55:45). IR (film): 3370, 2925, 1611, 1486, 1024 cm$^{-1}$. $^1$HNMR(CDCl$_3$/TMS): 7.00-7.35(m, Ar—H, 2H), 6.45-6.75(m, Ar—H, 2H), 5.14(d, 9b-H, J=8.0 Hz), 5.05(d, 9b-H, J=8.0 Hz), 4.76(d, 9b-H, J=5.2 Hz), 4.51(d, 9b-H, J=6.0 Hz), 3.99, 3.61, 3.35, 2.93, 2.66(m, 3H), 1.10-2.20(m, 31H), 0.88(m, 6H, CH$_3$). EIMS m/z 429(M$^+$), 272(100%), 130. HRMS m/z for C$_{28}$H$_{47}$NO$_2$ Calcd: 429.3607; Found: 429.3612.

2,3,3a,4,5,9b-hexahydro-2-phenyl-4-(3-hydroxy-3-phenylpropyl)furano[3,2-a]quinoline Via the general procedure 2, the titled compound was prepared in 51% yield. IR (film): 3368, 2940, 1610, 1494, 1028 cm$^{-1}$. $^1$HNMR(CDCl$_3$/TMS): 7.04-7.44(m, Ar—H, 12H), 6.78(m, Ar—H, 1H), 6.63(m, Ar—H, 1H), 5.39(d, 9b-H, J=8.0 Hz), 5.27(d, 9b-H, J=8.0 Hz), 5.01(d, 9b-H, J=6.4 Hz), 4.74(d, 9b-H, J=6.4 Hz), 5.06, 4.92 and 4.69 (m, 3H), 3.40, 3.08, 2.91 and 1.40-2.70(m, 8H). EIMS m/z 385(M$^+$), 250, 130, 77(100%). HRMS m/z for C$_{26}$H$_{27}$NO$_2$ Calcd: 385.2042; Found: 385.2040.

3,4,4a,5,6,10b-hexahydro-5-(4-hydroxybutyl)-2H-pyrano[3,2-c]quinoline

Via the general procedure 2, the titled compound was prepared in 89% yield (trans/cis=36:64). IR (film): 3379, 2934, 1608, 1494, 1065 cm$^{-1}$. $^1$HNMR (CDCl$_3$/TMS): cis-isomer, 7.36(d, 1H, Ar—H, J=7.6 Hz), 7.02(t, 1H, Ar—H, J=7.2 Hz), 6.72(t, 1H, Ar—H, J=7.2 Hz), 6.48(d, 1H, Ar—H, J=6.8 Hz), 5.05(d, 10b-H, J=5.6 Hz), 3.67(t, 2H, J=6.4 Hz), 3.58(m, 1H), 3.41(m, 2H), 2.04(m, 1H), 1.30-1.80(m, 10H). trans-isomer, 7.19(d, 1H, Ar—H, J=7.2 Hz), 7.02(t, 1H, Ar—H, J=7.2 Hz), 6.65(t, 1H, Ar—H, J=7.2 Hz), 6.50(d, 1H, Ar—H, J=6.8 Hz), 4.44(d, 10b-H, J=3.2 Hz), 3.91(m, 1H), 3.66(m, 3H), 3.58(m, 1H), 1.93(m, 1H), 1.30-1.80(m, 10H). EIMS m/z 261(M$^+$), 188(100%), 144. HRMS m/z for C$_{16}$H$_{23}$NO$_2$ Calcd: 261.1729; Found: 261.1717.

3,4,4a,5,6,10b-hexahydro-2-methyl-5-(4-hydroxypentyl)-2H-pyrano[3,2-c]quinoline Via the general procedure 2, the titled compound was prepared in 85% yield (trans/cis=40:60). IR (film): 3379, 2928, 1610, 1495, 1081 cm$^{-1}$. $^1$HNMR(CDCl$_3$/TMS): 7.35 and 7.14(m, Ar—H, 1H), 7.02(m, Ar—H, 1H), 6.65(m, Ar—H, 1H), 6.48(m, Ar—H, 1H), 5.09(d, 9b-H, J=5.6 Hz), 4.98(d, 9b-H, J=5.6 Hz), 4.49(d, 9b-H, J=4.4 Hz), 4.53(d, 9b-H, J=2.4 Hz), 3.77(m, 1H), 3.84(m, 1H), 3.50, 3.21 and 3.01(m, 2H), 1.25-2.20(m, 10H), 1.18(m, 6H, CH$_3$) EIMS m/z 289(M$^+$), 202(100%), 144. HRMS m/z for C$_{18}$H$_{27}$NO$_2$ Calcd: 289.2042; Found: 289.2039.

3,4,4a,5,6,10b-hexahydro-2-hexyl-5-(4-hydroxydecyl)-2H-pyrano[3,2-c]quinoline Via the general procedure 2, the titled compound was prepared in 45% yield (trans/cis=44:56). IR (film): 3383, 2927, 1608, 1494, 1083 cm$^{-1}$. $^1$HNMR(CDCl$_3$/TMS): 7.34, 7.15 and 7.03(m, Ar—H, 2H), 6.69 and 6.50(m, Ar—H, 2H), 5.10(d, 9b-H, J=6.4 Hz), 4.99(d, 9b-H, J=5.6 Hz), 4.61(d, 9b-H, J=5.6 Hz), 4.29(d, 9b-H, J=2.4 Hz), 3.65, 3.52, 3.34, 3.14 and 3.02(m, 3H), 2.60 and 2.44(m, 1H), 1.10-2.10(m, 30H), 0.88(m, 6H, CH$_3$). EIMS m/z 429(M$^+$), 272(100%), 144. HRMS m/z for C$_{28}$H$_{47}$NO$_2$ Calcd: 429.3607; Found: 429.3596.

3,4,4a,5,6,10b-hexahydro-2-phenyl-5-(4-hydroxy-4-phenylbutyl)-2H-pyrano[3,2-c]quinoline Via the general procedure 2, the titled compound was prepared in 48% yield. IR (film): 3402, 2936, 1604, 1494, 1026 cm$^{-1}$. $^1$HNMR(CDCl$_3$/TMS): 7.03-7.42(m, Ar—H, 12H), 6.70(m, Ar—H, 1H), 6.55(m, Ar—H, 1H), 5.15, 4.70 and 4.66(m, 3H), 3.80 and 3.06(m, 1H), 1.40-2.20(m, 11H). HRMS m/z for C$_{28}$H$_{31}$NO$_2$ Calcd: 413.2355; Found: 413.2348.

Example

Inhibition of Tumor Growth In vivo in Nude Mice

Representative peptide and non-peptide compounds having high in vitro cytotoxic activity are tested against implanted tumors in vivo. Athymic nude mice are implanted subcutaneously with either single cell suspensions (2 million SCLC cells or 1 million NSCLC cells) or with small fragments (3.times.3 mm) of tumors minced from previously grown nude mouse heterotransplants. On the seventh day after tumor implantation groups of 5 mice bearing implants are injected intraperitoneally daily with the compounds being tested at 1, 5, or 10 mg/kg/day; control animals are injected with an equal volume of isotonic saline. Tumor size is measured with a caliper three times per week.

Tumor volume is calculated by the formula:

$$\text{Volume(cc)} = \pi \times (\text{length}) \times (\text{width})^2 / 6$$

More information about the present invention can be found in our paper, incorporated herein by reference, entitled "InCl$_3$-Catalyzed Domino Reaction of Aromatic Amines with Cyclic Enol Ethers in Water: A Highly Efficient Synthesis of New 1,2,3,4-Tetrahydroquinoline Derivatives", *J. Org. Chem.* 2002, 67, 3969-3971.

REFERENCES 1. (a) Ramesh, M.; Moham, P. S.; Shanmugam, P. *Tetrahedron* 1984, 40, 4041. (b) Witherup, K. M.; Ransom, R. W.; Varga, S. L.; Pitzenberger, S. M.; Lotti, V. J.; Lumma, W. J. U.S. Pat. 1994, U.S. Pat. No. 5,288,725. (c) Perry, N. B.; Blunt, J. W.; McCombs, J. D.; Munro, M. H. G. *J. Org. Chem.* 1986, 51, 5476. (d) Williamson, N. M.; March, P. R.; Ward, A. D. *Tetrahedron Lett.* 1995, 36, 7721. (e) Johnson, J. V.; Rauckman, S.; Baccanari, P. D.; Roth, B. *J. Med. Chem.* 1989, 32, 1942. (f) Biller, S. A.; Misra, R. N. U.S. Pat. 1989, U.S. Pat. No. 4,843,082. (g) Mohamed, E. A. *Chem. Pap.* 1994, 48, 261; *Chem. Abstr.* 1995, 123, 9315. (h) Carling, R. W.; Leeson, P. D.; Moseley, A. M.; Baker, R.; Foster, A. C.; Grimwood, S.; Kemp, J. A.; Marshall, G. R. *J. Med. Chem.* 1992, 35, 1942; (i) Caling, R. W.; Leeson, P. D.; Moseley, A. M.; Smith, J. D.; Saywell, K.; Trickelbank, M. D.; Kemp, J. A.; Marshall, G. R.; Foster, A. C.; Grimwood, S. *Bioorg. Med. Chem. Lett.* 1993, 3, 65. (j) Cuny, G. D.; Hauske, J. D.; Hoemann, M. Z.; Rossi, R. F.; Xie, R. L. *PCT Int. Appl.* 1999, WO 9967238; *Chem. Abstr.* 1999, 132, 64182. (k) Hanada, K.; Furuya, K.; Inoguchi, K.; Miyakawa, M.; Nagata, N. *PCT Int. Appl.* 2001, WO 0127086; *Chem. Abstr.* 2001, 134, 295752.
2. Katritzky, A. R.; Rachwal, S.; Rachwal, B. *Tetrahedron* 1996, 52, 15031.
3. (a) Povarov, L. S. *Russ. Chem. Rev., Engl. Transl.* 1967, 36, 656. (b) Boger, D. L.; Weinreb, S. M. *Hetero Diels-Alder Methodology in Organic Synthesis* Academic: San Diego, 1987, Chapt. 2 and 9.
4. (a) Crousse, B.; Begue, J.; Bonnet-Delpon, D. *J. Org. Chem.* 2000, 65, 5009. (b) Mendoza, J. S. *PCT Int. Appl.* 1998, WO 9827093; *Chem. Abstr.* 1998, 129, 95393. (c) Makioka, Y.; Shindo, T.; Taniguchi, Y.; Takaki, K.; Fujiwara, Y. *Synthesis* 1995, 801. (d) Lucchini, V.; Prato, M.; Scorrano, G.; Stivanello, M.; Valle, G. *J. Chem. Soc., Perkin Trans.* 2 1992, 259. (e) Kametani, T.; Furuyama, H.; Fukuoka, Y.; Takeda, H.; Suzuki, Y.; Honda, T. *J. Heterocycl. Chem.* 1986, 23, 185. (f) Babu, G.; Perumal, P. T. *Tetrahedron Lett.* 1998, 39, 3225. (g) Sundararajan, G.; Prabagaran, N.; Varghese, B. *Org. Lett.* 2001, 3, 1973.

5. (a) Ma, Y., Qian, C.; Xie, M.; Sun, J. *J. Org. Chem.* 1999, 64, 6462. (b) Kobayashi, S.; Komiyama, S.; Ishitani, H. *Biotechnol. Bioeng.* 1998, 61, 23. (c) Kobayashi, S.; Nagayama, S. *J. Am. Chem. Soc.* 1996, 118, 8977.

6. A similar reaction was reported recently: $Dy(OTf)_3$ catalyzed formation of hexahydrofuro[3,2-c]quinolinesvia 2:1 coupling of dihydrofuran with substuted anilines. Batey, R. A.; Powell, D. A.; Acton, A.; Lough, A. J. Tetrohedron Lett., 2001, 7935.

7. (a) Woods, G. F., *Org. Synth. Coll. Vol.* 3. 470. (b) Schniepp, L. E; Geller, H. H, *J. Am. Chem. Soc.*, 1946, 68, 1646.

8. Boschi, A.; Chiappe, C; De Rubertis, A.; Ruasse, M. F. *J. Org. Chem.* 2000, 65, 8470.

9. (a) Schmitt, A.; Reiβig, H. U. *Chem. Ber.* 1995, 128, 871. (b) Winterfeldt, F. *Synthesis* 1975, 617. (c) Takacs, J. M.; Helle, M. A.; Seely, F. L. *Tetrahedron Lett.* 1986, 27, 1257.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of treating a cancer selected from the group consisting of lung cancer, CNS cancer, and breast cancer, by administering to a patient in need thereof a therapeutically effective amount of a compound having the formula:

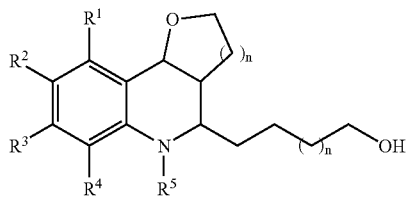

wherein $R^1$, $R^2$, $R^3$, $R^4$, and $R^5$ are each independently selected from the group consisting of hydrogen, alkyl, phenyl, cyano, carboxy, hydroxy, alkoxy, phenyloxy, chloro, bromo, fluoro, iodo, amino, alkylamino, dialkylamino, phenylamino, and diphenylamino; and the number n is 1 or 2; or a pharmaceutically acceptable salt thereof.

2. A method of treating a cancer selected from the group consisting of lung cancer, CNS cancer, and breast cancer by administering to a patient in need thereof a therapeutically effective amount of a compound having the formula:

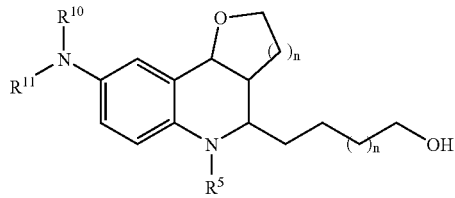

wherein:

$R^5$, $R^{10}$, and $R^{11}$ are each, independently, selected from the group consisting of hydrogen, alkyl, and phenyl; and n in each occurrence may be the same or different and is 1 or 2;

or a pharmaceutically acceptable salt thereof.

3. The method of claim 2 wherein the compound is in the form of a pharmaceutically acceptable salt.

4. The method of claim 2 wherein the compound is selected from the group consisting of:

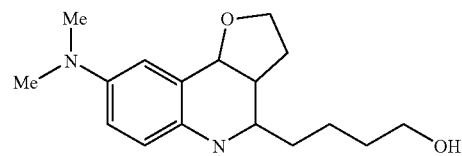

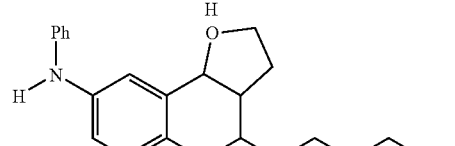

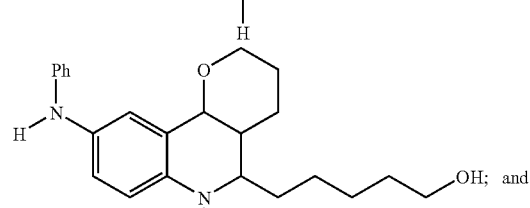

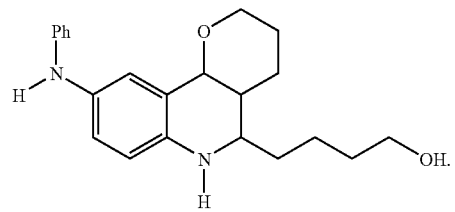

* * * * *